US011691142B2

(12) United States Patent
Gorin et al.

(10) Patent No.: US 11,691,142 B2
(45) Date of Patent: Jul. 4, 2023

(54) AUTOPLATELET CARTRIDGE DEVICE

(71) Applicant: CA CASYSO GmbH, Basel (CH)

(72) Inventors: Michael M. Gorin, Incline Village, NV (US); Robert S. Hillman, San Diego, CA (US); Cory Lee McCluskey, Encinitas, CA (US); Hubert Martin Schwaiger, Munich (DE)

(73) Assignee: CA CASYSO GMBH, Basel (CH)

( * ) Notice: Subject to any disclaimer, the term of this patent is extended or adjusted under 35 U.S.C. 154(b) by 444 days.

(21) Appl. No.: 17/064,532

(22) Filed: Oct. 6, 2020

(65) Prior Publication Data

US 2021/0016270 A1 Jan. 21, 2021

Related U.S. Application Data

(62) Division of application No. 15/648,345, filed on Jul. 12, 2017, now Pat. No. 10,843,185.

(51) Int. Cl.
*B01L 3/00* (2006.01)
*G01N 33/86* (2006.01)
(Continued)

(52) U.S. Cl.
CPC ......... *B01L 3/502* (2013.01); *B01L 3/502715* (2013.01); *B01L 3/502738* (2013.01);
(Continued)

(58) Field of Classification Search
CPC .............. B01L 3/502; B01L 3/502715; B01L 3/502738; B01L 3/527; B01L 7/00;
(Continued)

(56) References Cited

U.S. PATENT DOCUMENTS 2,555,937 A 6/1951 Rosenthal et al.
2,995,425 A 8/1961 Fuhrmann
(Continued)

FOREIGN PATENT DOCUMENTS

CN 1853104 A 10/2006
CN 1985168 A 6/2007
(Continued)

OTHER PUBLICATIONS

China National Intellectual Property Administration, Office Action, CN Patent Application No. 201880056029.8, dated Mar. 22, 2021, 13 pages.
(Continued)

*Primary Examiner* — Samuel P Siefke
(74) *Attorney, Agent, or Firm* — Burns & Levinson LLP

(57) ABSTRACT

Embodiments of a platelet testing system include an analyzer console device and a blood testing cartridge configured to releasably install into the console device. The cartridge device is configured with one or more measuring chambers and one or more mixing chambers that are fluidically connected within the cartridge device that enable the mixing of saline and a blood sample to a desired dilution. Additionally, the cartridge device is further configured with a cartridge slider that provides a reagent bead to the saline and blood mixture at a desired time. As such, one or more platelet activation assays can be conducted by measuring, through cartridge electrodes of the cartridge device, the detectable changes in platelet activity within the blood and saline mixture.

20 Claims, 15 Drawing Sheets

(51) Int. Cl.
  *G01N 35/00*       (2006.01)
  *G01N 15/06*       (2006.01)
  *B01L 7/00*        (2006.01)
  *G01N 15/00*       (2006.01)

(52) U.S. Cl.
  CPC ............... *B01L 3/527* (2013.01); *B01L 7/00* (2013.01); *G01N 15/0656* (2013.01); *G01N 33/86* (2013.01); *G01N 35/00722* (2013.01); *B01L 2200/0689* (2013.01); *B01L 2200/147* (2013.01); *B01L 2300/041* (2013.01); *B01L 2300/0645* (2013.01); *B01L 2300/0809* (2013.01); *B01L 2300/0867* (2013.01); *B01L 2300/123* (2013.01); *B01L 2300/161* (2013.01); *B01L 2400/0633* (2013.01); *B01L 2400/0638* (2013.01); *G01N 2015/0084* (2013.01); *G01N 2015/0092* (2013.01); *G01N 2035/0091* (2013.01); *G01N 2035/00356* (2013.01)

(58) Field of Classification Search
  CPC ....... B01L 2200/0689; B01L 2200/147; B01L 2300/041; B01L 2300/0645; B01L 2300/0809; B01L 2300/0867; B01L 2300/123; B01L 2300/161; B01L 2400/0633; B01L 2400/0638; B01L 2200/028; B01L 2300/046; B01L 2300/16; G01N 15/0656; G01N 33/86; G01N 35/00722; G01N 2015/0084; G01N 2015/0092; G01N 2035/00356; G01N 2035/0091
  See application file for complete search history.

(56) References Cited

U.S. PATENT DOCUMENTS

| | | | |
|---|---|---|---|
| 3,714,815 | A | 2/1973 | Hartert |
| 3,803,903 | A | 4/1974 | Lin |
| 3,903,903 | A | 9/1975 | Matsumura |
| 4,148,216 | A | 4/1979 | Do et al. |
| 4,193,293 | A | 3/1980 | Cavallari |
| D260,428 | S | 8/1981 | Fekete |
| 4,319,194 | A | 3/1982 | Cardinal et al. |
| 4,599,219 | A | 7/1986 | Cooper et al. |
| 4,726,220 | A | 2/1988 | Feier et al. |
| 4,752,449 | A | 6/1988 | Jackson et al. |
| 4,753,776 | A | 6/1988 | Hillman et al. |
| 4,756,884 | A | 7/1988 | Hillman et al. |
| 4,765,180 | A | 8/1988 | Clifton |
| 4,767,600 | A | 8/1988 | Vicario |
| D302,294 | S | 7/1989 | Hillman |
| 4,868,129 | A | 9/1989 | Gibbons et al. |
| D305,360 | S | 1/1990 | Fechtner |
| 4,948,961 | A | 8/1990 | Hillman et al. |
| 4,956,089 | A | 9/1990 | Hurst |
| 4,963,498 | A | 10/1990 | Hillman et al. |
| 5,009,316 | A | 4/1991 | Klein |
| 5,028,142 | A | 7/1991 | Ostoich et al. |
| 5,077,017 | A | 12/1991 | Gorin et al. |
| 5,104,813 | A | 4/1992 | Besemer et al. |
| D327,743 | S | 7/1992 | Frenkel et al. |
| 5,162,237 | A | 11/1992 | Messenger et al. |
| 5,164,598 | A | 11/1992 | Hillman et al. |
| 5,207,988 | A | 5/1993 | Lucas |
| 5,222,808 | A | 6/1993 | Sugarman et al. |
| 5,223,219 | A | 6/1993 | Subramanian et al. |
| 5,223,227 | A | 6/1993 | Zuckerman |
| 5,287,732 | A | 2/1994 | Sekiguchi |
| D347,067 | S | 5/1994 | Shartle et al. |
| 5,447,440 | A | 9/1995 | Davis et al. |
| 5,531,102 | A | 7/1996 | Brookfield et al. |
| 5,777,212 | A | 7/1998 | Sekiguchi et al. |
| 5,777,215 | A | 7/1998 | Calatzis et al. |
| 5,788,928 | A | 8/1998 | Carey et al. |
| 5,902,937 | A | 5/1999 | Amrani et al. |
| 6,012,712 | A | 1/2000 | Bernstein |
| 6,066,243 | A | 5/2000 | Anderson et al. |
| 6,200,532 | B1 | 3/2001 | Wu et al. |
| 6,448,024 | B1 | 9/2002 | Bruegger |
| 6,537,819 | B2 | 3/2003 | Cohen et al. |
| 6,613,286 | B2 | 9/2003 | Braun et al. |
| D481,133 | S | 10/2003 | Blouin et al. |
| D482,454 | S | 11/2003 | Gebrian |
| 6,662,031 | B1 | 12/2003 | Khalil et al. |
| 6,699,718 | B1 | 3/2004 | Bruegger |
| 6,750,053 | B1 | 6/2004 | Widrig Opalsky et al. |
| 6,838,055 | B2 | 1/2005 | Sando et al. |
| 6,942,836 | B2 | 9/2005 | Freudenthal et al. |
| 6,951,127 | B1 | 10/2005 | Bi |
| 6,979,569 | B1 | 12/2005 | Carver et al. |
| 7,399,637 | B2 | 7/2008 | Wright et al. |
| 7,412,877 | B2 | 8/2008 | Bi |
| 7,422,905 | B2 | 9/2008 | Clague et al. |
| 7,491,175 | B2 | 2/2009 | Ruether et al. |
| 7,497,997 | B2 | 3/2009 | Glezer et al. |
| 7,524,670 | B2 | 4/2009 | Cohen et al. |
| 7,595,169 | B2 | 9/2009 | Swaim et al. |
| 7,732,213 | B2 | 6/2010 | Cohen et al. |
| 7,745,223 | B2 | 6/2010 | Schubert et al. |
| 7,811,792 | B2 | 10/2010 | Cohen et al. |
| 7,901,629 | B2 | 3/2011 | Calatzis et al. |
| 7,947,505 | B2 | 5/2011 | Kawasaki et al. |
| 7,951,606 | B2 | 5/2011 | Pei et al. |
| 8,003,401 | B2 | 8/2011 | Tonnessen et al. |
| D645,973 | S | 9/2011 | Hoenes |
| 8,110,392 | B2 | 2/2012 | Battrell et al. |
| 8,168,442 | B2 | 5/2012 | Petersen et al. |
| 8,383,045 | B2 | 2/2013 | Schubert et al. |
| 8,448,499 | B2 | 5/2013 | Schubert et al. |
| 8,857,244 | B2 | 10/2014 | Schubert et al. |
| 9,061,280 | B2 | 6/2015 | Tanaami et al. |
| D737,993 | S | 9/2015 | Tan et al. |
| 9,272,280 | B2 | 3/2016 | Viola et al. |
| 9,285,377 | B2 | 3/2016 | Schubert et al. |
| D777,343 | S | 1/2017 | Gorin et al. |
| 2002/0081741 | A1 | 6/2002 | Braun et al. |
| 2002/0177958 | A1 | 11/2002 | Widrig Opalsky et al. |
| 2003/0073244 | A1 | 4/2003 | Cohen et al. |
| 2004/0072278 | A1 | 4/2004 | Chou et al. |
| 2004/0089616 | A1 | 5/2004 | Kellogg et al. |
| 2004/0131500 | A1 | 7/2004 | Chow |
| 2005/0136541 | A1 | 6/2005 | De Haan |
| 2005/0233460 | A1 | 10/2005 | Clague et al. |
| 2005/0233466 | A1 | 10/2005 | Wright et al. |
| 2007/0059840 | A1 | 3/2007 | Cohen et al. |
| 2007/0099290 | A1 | 5/2007 | Iida et al. |
| 2007/0140902 | A1 | 6/2007 | Calatzis et al. |
| 2007/0243105 | A1 | 10/2007 | Kratzer et al. |
| 2008/0026476 | A1 | 1/2008 | Howell et al. |
| 2008/0160500 | A1 | 7/2008 | Fuller et al. |
| 2008/0194041 | A1 | 8/2008 | Guirguis |
| 2008/0227217 | A1 | 9/2008 | Yamamoto et al. |
| 2008/0251383 | A1 | 10/2008 | Sobek et al. |
| 2008/0261261 | A1 | 10/2008 | Grimes et al. |
| 2008/0297169 | A1 | 12/2008 | Greenquist et al. |
| 2009/0130645 | A1 | 5/2009 | Schubert et al. |
| 2009/0181411 | A1 | 7/2009 | Battrell et al. |
| 2010/0056383 | A1 | 3/2010 | Ririe et al. |
| 2010/0154520 | A1 | 6/2010 | Schubert et al. |
| 2010/0184201 | A1 | 7/2010 | Schubert et al. |
| 2011/0201099 | A1 | 8/2011 | Anderson et al. |
| 2011/0237913 | A1 | 9/2011 | Schubert et al. |
| 2011/0252352 | A1 | 10/2011 | Viola et al. |
| 2012/0084022 | A1 | 4/2012 | Giovangrandi et al. |
| 2012/0294767 | A1 | 11/2012 | Viola et al. |
| 2012/0329082 | A1 | 12/2012 | Viola et al. |
| 2013/0137172 | A1 | 5/2013 | Ririe et al. |
| 2013/0270113 | A1 | 10/2013 | Huang |
| 2013/0323846 | A1 | 12/2013 | Schubert et al. |
| 2013/0323847 | A1 | 12/2013 | Schubert et al. |
| 2013/0323848 | A1 | 12/2013 | Schubert et al. |

(56) References Cited

U.S. PATENT DOCUMENTS

| | | |
|---|---|---|
| 2013/0333448 A1 | 12/2013 | Schubert et al. |
| 2014/0004613 A1 | 1/2014 | Goldstein |
| 2014/0271409 A1 | 9/2014 | Knight et al. |
| 2014/0328732 A1 | 11/2014 | Delmenico et al. |
| 2015/0253271 A1 | 9/2015 | Giridhar et al. |
| 2015/0316460 A1 | 11/2015 | Redl et al. |
| 2016/0091483 A1 | 3/2016 | McCluskey et al. |
| 2016/0091509 A1 | 3/2016 | Di Tullio et al. |
| 2016/0091511 A1 | 3/2016 | Di Tullio et al. |
| 2016/0091514 A1 | 3/2016 | Gorin et al. |
| 2016/0091515 A1 | 3/2016 | Gorin et al. |
| 2016/0091516 A1 | 3/2016 | Gorin et al. |
| 2016/0091517 A1 | 3/2016 | Gorin et al. |
| 2016/0195557 A1 | 7/2016 | Schubert et al. |
| 2016/0313357 A1 | 10/2016 | Viola et al. |
| 2016/0361715 A1 | 12/2016 | Shi et al. |
| 2016/0377638 A1 | 12/2016 | Bels et al. |
| 2017/0254318 A1 | 9/2017 | Lee et al. |
| 2018/0133714 A1 | 5/2018 | Wo et al. |

FOREIGN PATENT DOCUMENTS

| | | |
|---|---|---|
| CN | 101195112 A | 6/2008 |
| CN | 101301632 A | 11/2008 |
| CN | 101563562 A | 10/2009 |
| CN | 102265151 | 11/2011 |
| CN | 103170377 A | 6/2013 |
| CN | 103175950 A | 6/2013 |
| CN | 103217401 A | 7/2013 |
| CN | 104204787 A | 12/2014 |
| CN | 104903728 A | 9/2015 |
| DE | 2740932 A1 | 11/1978 |
| DE | 10135569 A1 | 2/2003 |
| DE | 202014002289 U1 | 9/2014 |
| EP | 0404456 A2 | 12/1990 |
| EP | 1367392 A1 | 12/2003 |
| EP | 1394546 A1 | 3/2004 |
| EP | 1627725 A2 | 2/2006 |
| EP | 1884778 A1 | 2/2008 |
| EP | 1901065 A1 | 3/2008 |
| EP | 2208996 A1 | 7/2010 |
| EP | 2202517 B1 | 8/2012 |
| EP | 3001196 A2 | 3/2016 |
| GB | 2257256 A | 1/1993 |
| JP | 1971-004947 A | 11/1971 |
| JP | 1987-140047 A | 6/1987 |
| JP | 1991-031764 A | 2/1991 |
| JP | 1997-159596 A | 6/1997 |
| JP | 09-507580 A | 7/1997 |
| JP | 2001-516880 A | 10/2001 |
| JP | 2005-534895 A | 11/2005 |
| JP | 2006-053142 A | 2/2006 |
| JP | 2007-532878 A | 11/2007 |
| JP | 2008-302322 A | 12/2008 |
| JP | 2010-078575 A | 4/2010 |
| JP | 2010-266453 A | 11/2010 |
| JP | 2011-174952 A | 9/2011 |
| JP | 2012-513582 A | 6/2012 |
| JP | 2012-515340 A | 7/2012 |
| JP | 2013-524176 A | 6/2013 |
| JP | 2014-010109 A | 1/2014 |
| JP | 2015-045642 A | 3/2015 |
| JP | 2016-118530 A | 6/2016 |
| WO | WO 1989/006803 A1 | 7/1989 |
| WO | WO 96/38730 A1 | 12/1996 |
| WO | WO 1999/014595 A1 | 3/1999 |
| WO | WO 2002/050535 A1 | 6/2002 |
| WO | WO 2002/063273 A2 | 8/2002 |
| WO | WO 2005/106467 A1 | 11/2005 |
| WO | WO 2006/091650 A1 | 8/2006 |
| WO | WO 2006/126290 A1 | 11/2006 |
| WO | WO 2006/137334 A1 | 12/2006 |
| WO | WO 2007/047961 A2 | 4/2007 |
| WO | WO 2008/075181 A2 | 6/2008 |
| WO | WO 2008/093216 A1 | 8/2008 |
| WO | WO 2009/073851 A1 | 6/2009 |
| WO | WO 2010/072620 A1 | 7/2010 |
| WO | WO 2011/117017 A1 | 9/2011 |
| WO | WO 2013/172003 A1 | 11/2013 |
| WO | WO 2014/115478 A1 | 7/2014 |
| WO | WO 2014/162285 A1 | 10/2014 |
| WO | WO 2014/172243 A1 | 10/2014 |
| WO | WO 2016/196236 | 12/2016 |
| WO | WO 2014/103744 A1 | 1/2017 |
| WO | WO 2017/096284 A1 | 6/2017 |

OTHER PUBLICATIONS

European Patent Office, European Extended Search Report and Opinion, EP Patent Application No. 18831324.1, dated Mar. 17, 2021, eight pages.
China National Intellectual Property Administration, Office Action, CN Patent Application No. 201880056029.8, dated Jul. 1, 2021, eight pages.
United States Office Action, U.S. Appl. No. 16/572,567, dated Sep. 3, 2021, ten pages.
Anonymous: Rotem delta Whole Blood Haemostasis System using Thromboelastometry US Operating Manual,: [retrieved on Oct. 30, 2015], Retrieved from the internet: <URL: http://www.sfgh-poct.org/wp-content/uploads/2013/02/ROTEM-delta-US-Operat- ing-Manual-Part-12.pdf>, Sep. 2012.
Calatzis et al., "Strategies to Assess Individual Susceptibility to abciximab Therapy Using a New Functional Assay," Annals of Hematology, (Berlin, DE) vol. 76, No. Suppl 1, p. A61, XP009097526, 1998.
Chakroun et al., "The influence of fibrin polymerization and platelet-mediated contractile forces on citrated whole blood thromboelastography profile," Thromb Haemost., 95(5):822-828, May 2006.
China National Intellectual Property Administration, Office Action, CN Patent Application No. 201880056029.8, dated Sep. 15, 2020, 12 pages (with concise explanation of relevance).
Chinese Office Action (OA) for App. No. 200980151858.5 dated May 21, 2013, 16 pgs.
Chinese Office Action for App. No. 200980151858.5 dated Feb. 14, 2014, 4 pgs.
European Extended search report for App No. 13167983.9, dated Nov. 6, 2013, 3 pgs.
European Office Action for App. No. 08172769.5, dated Jun. 1, 2011, 12 pgs.
European Office Action for App. No. 12179576.9, dated May 22, 2013, 10 pgs.
European Office Action for App. No. 13167979.7, dated Nov. 15, 2016, 8pgs.
European Office Action for Application No. 13163014.7, dated Mar. 24, 2014, 12 pages.
European Patent Office, Extended European Search Report and Opinion, European Patent Application No. 16871654.6, dated May 27, 2019, 7 pages.
European Patent Office, Extended European Search Report and Opinion, European Patent Application No. 17847520.8, dated Feb. 27, 2020, seven pages.
European Search Report and Opinion for Application No. 15187347.8, dated Jun. 1, 2016 (16 Pages).
Extended European Search Report, European Patent Office, European Patent Application No. 18193752.5, dated May 13, 2019, 13 pages.
First Office Action with concise explanation of relevance, Chinese Patent Application No. 201680074338.9, dated Feb. 3, 2019, 5 pages.
Greilich et al., "Near-site monitoring of the antiplatelet drug abciximab using the Hemodyne analyzer and modified thrombelastograph," J Cardiothorac Vase Anesth., 13(1 ):58-64, Feb. 1999.
Hartert, "Blood Coagulation Studies with Thromboelastography—A New Research Method," Klin Wochenschrift 26:577-583, Oct. 1948 [English translation].
HealthPACT,"Rotational thromboelastometry (ROTEM)—targeted therapy for coagulation management in patitnets with massive bleeding," "Health Policy Advisory Committee on Technology.

(56) References Cited

OTHER PUBLICATIONS

Retrieved from the Internet: <URL:https://www.heath.qld.gov.au/healthpact/docs/briefs/WP024.pdg>-, 30 pages, Nov. 2012".
Japan Patent Office, Notification of Reasons for Refusal, JP Patent Application No. 2019-001775, dated Jan. 31, 2020, 13 pages.
Japan Patent Office, Office Action, Japanese Patent Application No. 2018-528982, dated Jul. 2, 2019, 14 pages.
Japan Patent Office, Official Notice of Rejection, JP Patent Application No. 2020-501278, dated Jul. 14, 2020, eight pages.
Japanese Notification for Refusal for Application No. 2011-541392, dated Jun. 14, 2013, 4 pages.
Japanese notification of refusal for Ap. No. 2014-165975, dated Jul. 17, 2015, 8 pgs.
Japanese Office Action, Japanese Application No. 2015-191180, dated Nov. 17, 2017, 9 pages.
Kawasaki et al., "The effects of vasoactive agents, platelet agonists and anticoagulation on thrombelastography," ActaAnaesthesiol Scand., 51(9):1237-1244, Oct. 2007.
Khurana et al., "Monitoring platelet glycoprotein lib/IIIa-fibrin interaction with tissue factor-activated thromboelastography," J Lab Clin Med., 130(4):401-411, Oct. 1997.
Korean Office Action for Application No. 1020117017187, dated Mar. 28, 2016, 11 pages.
Korean Office Action for Application No. 1020167029191, dated Nov. 17, 2016, 5 pages.
Lang et al., "Evaluation of the new device ROTEM platelet" [retrieved on Oct. 28, 2015], Retrieved from the internet: <URL: https://www.rotem.de/wp-content/uploads/2014-09-Lang-et-al-2014.pdf>, Jan. 1, 2014.
National Intellectual Property Administration of China, Office Action, Chinese Patent Application No. 2016800743389, dated Aug. 12, 2019, 15 pages.
Nield et al., "MRI-based blood oxygen saturation measurements in infants and children with congenital heart disease," Pediatr Radiol., 32(7):518-522. Epub Apr. 16, 2002.
Nielsen et al., "Evaluation of the contribution of platelets to clot strength by thromboelastography in rabbits: the role of tissue factor and cytochalasin D," Anesth Anafa., 91(1):35-39, Jul. 2000.
Noon et al., "Reduction of blood trauma in roller pumps for long-term perfusion" World J Surg., 9(1):65-71, Feb. 1985.
Notification of Reasons for Refusal for Application No. 2015-132034, dated Jul. 29, 2016, 5 pages.
Novotny et al., "Platelets secrete a coagulation inhibitor functionally and antigenically similar to the lipoprotein associated coagulation inhibitor," Blood, 72(6):2020-2025, Dec. 1988.
Partial European search report, European Patent Application No. 18193752.5, dated Feb. 12, 2019, 15 pages.
PCT International Preliminary report on patentability for PCT/EP2009/067181, dated Jun. 29, 2011, 9 pgs.
PCT International search report and written opinion for Ap. No. PCT/EP2009/067181, dated Mar. 22, 2010, 12 pgs.
PCT International Search Report and Written Opinion, PCT Application No. PCT/US16/34501, dated Aug. 31, 2016, 17 pages.
PCT International Search Report and Written Opinion, PCT Application No. PCT/US16/64800, dated Feb. 16, 2017, 14 pages.
PCT International Search Report and Written Opinion, PCT Application No. PCT/US18/40120, dated Sep. 20, 2018, 13 pages.
PCT International Search Report and Written Opinion, PCT Application No. PCT/US2016/064790, dated Feb. 15, 2017, 17 pages.
PCT International Search Report and Written Opinion, PCT Application No. PCT/US2016/064797, dated Feb. 15, 2017, 16 pages.
PCT International Search Report and Written Opinion, PCT Application No. PCT/US2016/064806, dated Feb. 15, 2017, 18 pages.
PCT International Search Report and Written Opinion, PCT Application No. PCT/US2016064797, dated May 27, 2019, 7 pages.
PCT International Search Report and Written Opinion, PCT Application No. PCT/US2017/049505, dated Nov. 2, 2017, 17 pages.
Prisco and Paniccia, "Point-of-Care Testing of Hemostasis in Cardiac Surgery", Thromb J., 1(1):1, May 6, 2003.
Rodzynek et al., "The transfer test: a new screening procedure for thrombotic diseases," J Surg Res., 35(3):227-233, Sep. 1983.
ROTEM.RTM. "When Minutes Count to Stop the Bleeding," Pentapharm GmbH, www.rotem.de, 6 pages, Jun. 2007. [brochure].
ROTEM.RTM. delta, "Targeted therapy stops the bleeding," 6 pages, Jan. 6, 2014, [brochure].
ROTEM.RTM. delta, "Whole Blood Haemostasis System using Thromboelastomerty Operating Manual," 164 pages, Nov. 17, 2014 [brochure].
ROTEM.RTM., "Targeted therapy for coagulation management in patients with massive bleeding," https://www.health.qld.gov.au/_data/assets/pdf_file/0023/427145/wp024.pdf- , Nov. 2012, 30 pages, [brochure].
Rugeri et al., "Diagnosis of early coagulation abnormalities in trauma patients by rotation thrombelastography," J Thromb Haemost., 5(2):289-295, Epub Nov. 16, 2006.
Salooja and Perry, "Thrombelastography," Blood Coagul Fibrinolysis, 12(5):327-37, Jul. 2001.
Shore-Lesserson et al., "Thromboelastography-guided transfusion algorithm reduces transfusions in complex cardiac surgery," Anesth Analg., 88(2):312-319, Feb. 1999.
Soria et al., "Fibrin stabilizing factor (F XIII) and collagen polymerization," Experientia, 31(11):1355-1357, Nov. 15, 1975.
Spannagl et al., "Point-of-Care Analysis of the Homostatic System," Laboratoriumsmedizin, (Kirchheim, DE), 26(1-2):68-76, Feb. 2002.
Srinivasa et al., "Thromboelastography: Where Is It and Where Is It Heading?" Int'l Anesthesiology Clinics, 39(1 ):35-49, Winter 2001.
Tanaka et al., "Thrombin generation assay and viscoelastic coagulation monitors demonstrate differences in the mode of thrombin inhibition between unfractionated heparin and bivalirudin," Anesth Analg., 105(4):933-939, Oct. 2007.
United States Office Action, U.S. Appl. No. 14/958,889, dated Sep. 13, 2019, 18 pages.
United States Office Action, U.S. Appl. No. 15/648,345, dated Jan. 22, 2020, nine pages.

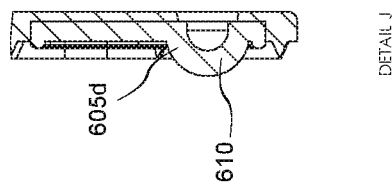
FIG. 6C
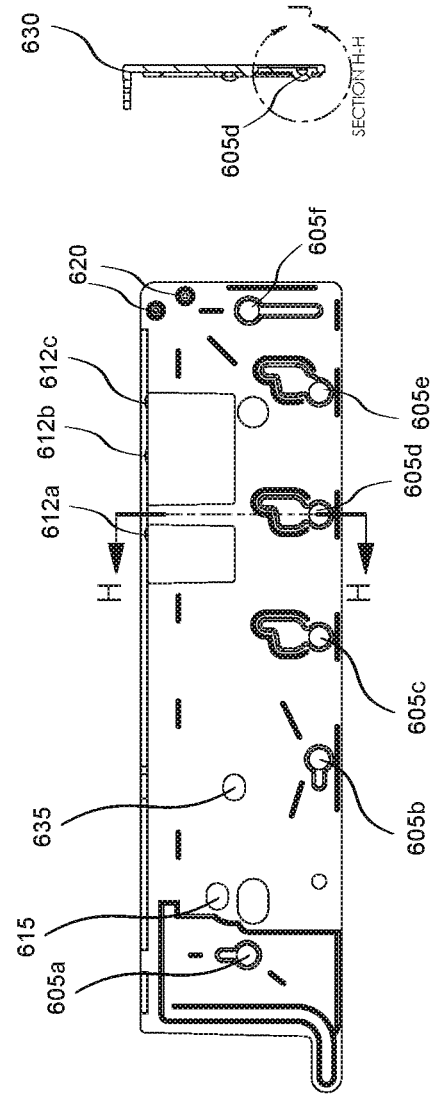
FIG. 6B
FIG. 6A
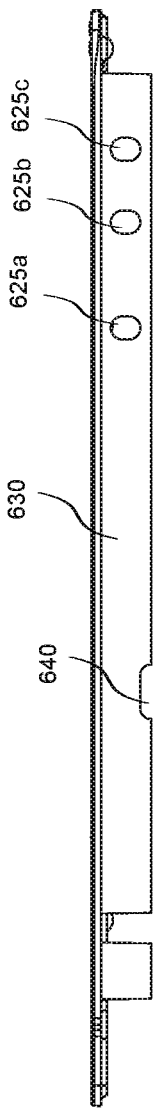
FIG. 6D

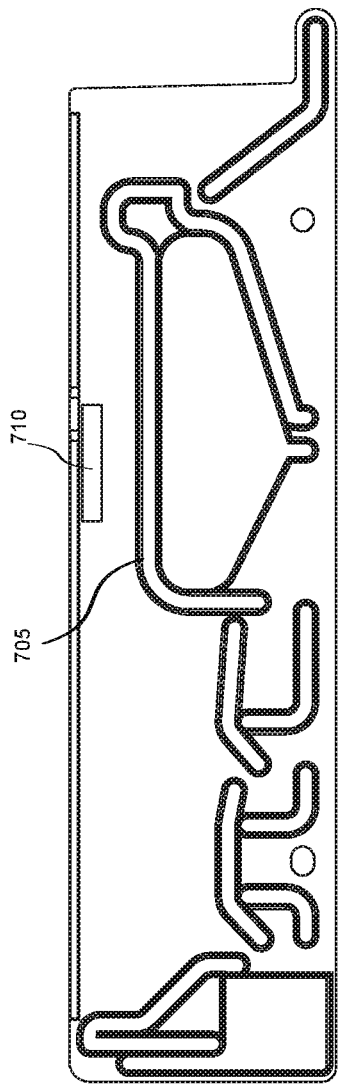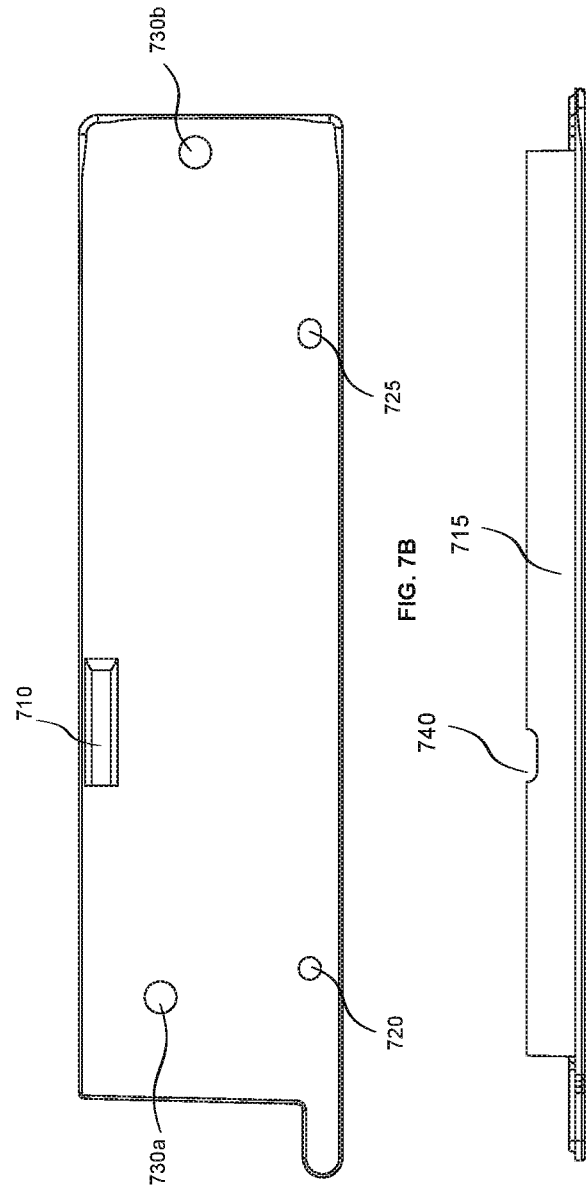

SECTION L-L

SECTION L-L

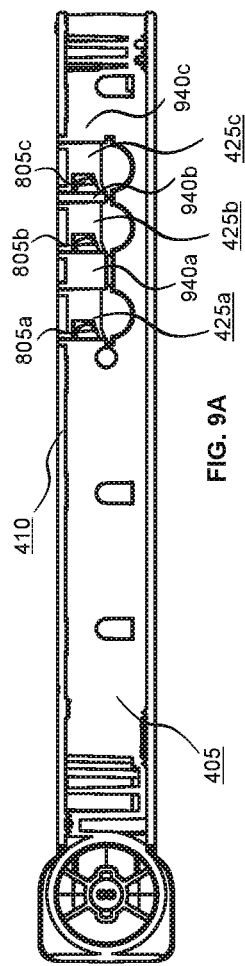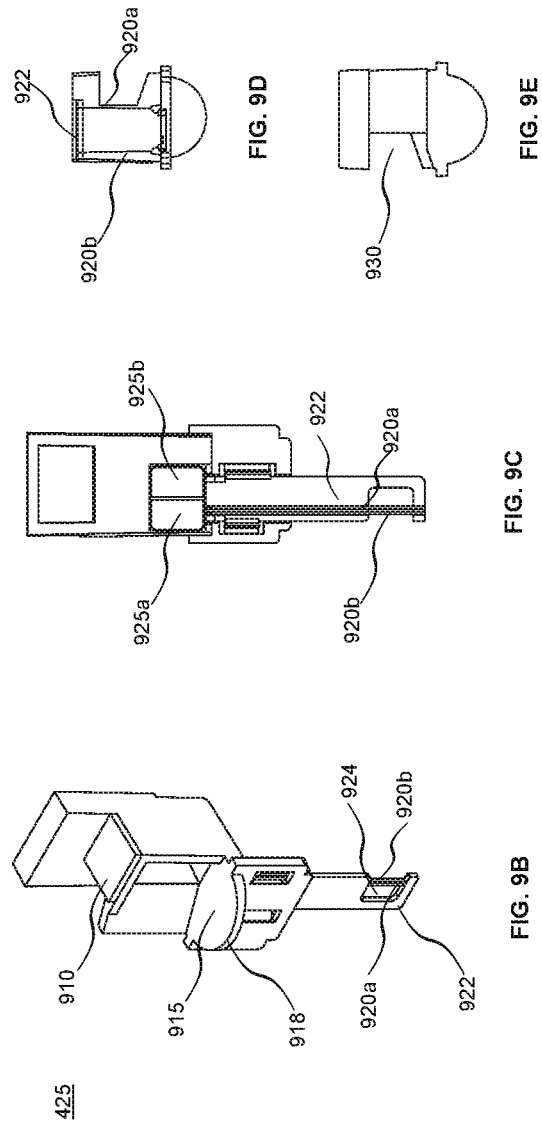

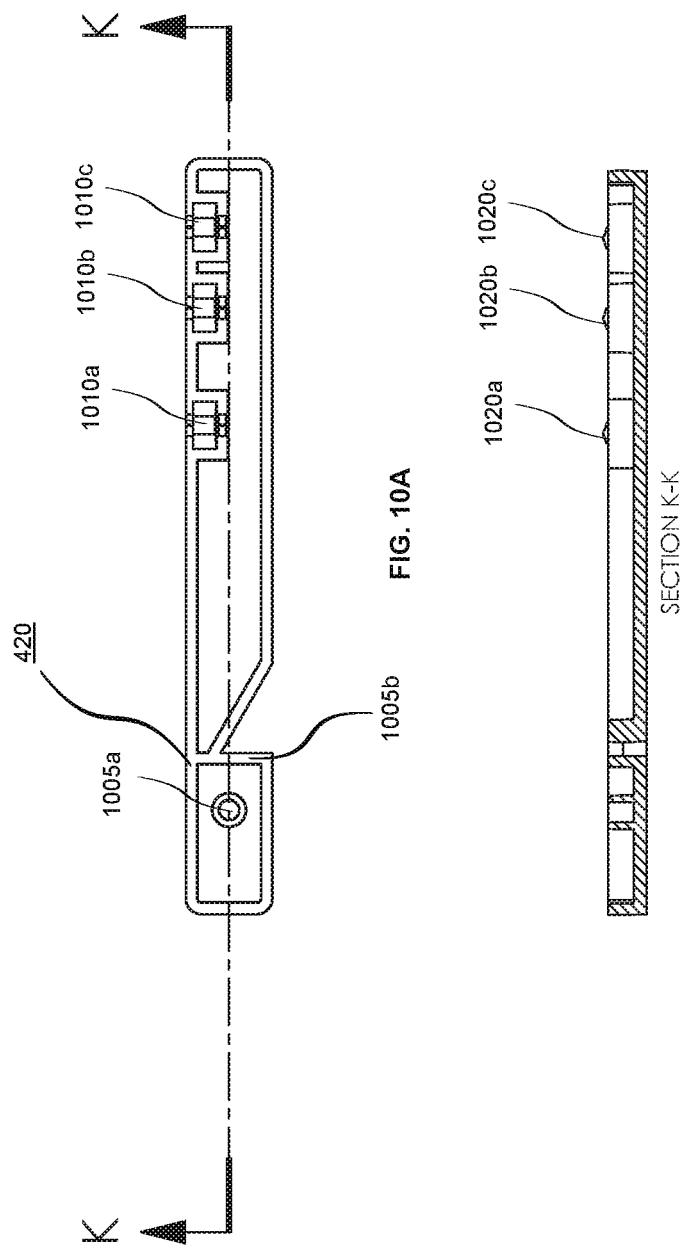

SECTION L-L

SECTION L-L

AUTOPLATELET CARTRIDGE DEVICE

CROSS REFERENCE TO RELATED APPLICATIONS

The present application is divisional application of Ser. No. 15/648,345, "Autoplatelet Cartridge Device," filed Jul. 12, 2017, the entire disclosure of which is hereby incorporated by reference, in its entirety, for all purposes.

TECHNICAL FIELD

This disclosure relates to systems and method for testing characteristics of a blood sample, and more specifically, to a cartridge system for characterizing platelet activity of a blood sample.

BACKGROUND

Hemostasis is the human body's response to blood vessel injury and bleeding. Hemostasis involves a coordinated effort between platelets and numerous blood clotting proteins (or clotting factors), resulting in the formation of a blood clot and the subsequent stoppage of bleeding.

Various methods have been introduced to assess the potential of platelets to form an adequate clot and to determine the clot's stability. Common laboratory tests such as thrombocyte counts or the determination of fibrin concentration provide information on whether the tested component is available in sufficient amount, but some of those tests may not answer the question of whether the tested component works properly under physiological conditions. Other laboratory tests work on blood plasma, which may impose additional preparation steps and additional time beyond what is preferred, for example, in the point-of-care context or in a surgical theater during a surgical operation.

Another group of tests involve assessing the potential of platelets from a blood sample to form an adequate clot. As an example, the clot firmness (or other parameters dependent thereon) is determined over a period of time from the formation of the first fibrin fibers until the dissolution of the blood clot by fibrinolysis. Blood clot firmness is a functional parameter which contributes to hemostasis in vivo, as a clot must resist blood pressure and shear stress at the site of vascular injury or incision. In many cases, clot firmness may result from multiple interlinked processes including coagulation activation, thrombin formation, fibrin formation and polymerization, platelet activation, and fibrin-platelet interaction.

To isolate and test particular functions of thrombocytes, fibrinogen, platelets, and other factors in a blood sample, reagent compounds can be mixed with the blood sample to activate or inhibit their activity in the blood sample. In some commercially available point-of-care blood testing systems, liquid reagents are injected into a disposable plastic cup containing a blood sample, and the cup is then engaged by the control console of the blood testing system to evaluate characteristics of the coagulation/clotting of the blood sample. As part of the test process, the system requires manual intervention by the operator for each of the assays, for example, when pipettes are used by an operator for the dispensing and measuring of the reagents, blood, and mixed samples. Manual intervention is often inaccurate and may often result in manual error and is, therefore, an undesirable method of assaying activity of components in a blood sample.

SUMMARY

Some embodiments of a system for testing characteristics of a blood sample (which, as used herein, should be understood to include blood or derivatives of blood such as plasma) can include a cartridge configured to mate with a control console and receive a blood sample for a point-of-care whole blood coagulation analysis. In particular circumstances, the cartridge is configured to interact with the control console so as to perform a number of automated transport and testing operations on portions of the blood sample so as to provide reliable and prompt results indicative of a patient's blood characteristics at the point-of-care. For example, the system can serve as an automated system for providing detailed and prompt results of blood coagulation characteristics in response to receiving a cartridge (and blood sample at the cartridge) and an indication from an operator to begin the automated testing process.

In some embodiments, the system includes a reusable analyzer console and one or more single-use cartridge components configured to mate with the console. In one example, to operate the system, a user inserts the cartridge into the analyzer console and, when prompted by the analyzer console, inserts a blood collection tube (containing a whole blood sample) into a receiver portion of the cartridge. Thereafter, the analyzer console automatically performs (without requiring further user interaction with the cartridge or the blood sample) the testing, and displays the results on a graphical display using qualitative graphical representations and quantitative parameters. In this particular example, no manual pipetting, mixing, or handling of reagents by the user is needed. In some embodiments, three or more assays are automatically performed on the blood sample using a single cartridge device. Such assays provide information on the whole kinetics of hemostasis, such as clotting time, clot formation, clot stability, and lysis; moreover, such information can be promptly output from a user interface of the system to provide reliable and prompt results indicative of a patient's blood characteristics at the point-of-care (e.g., while the patient is in a surgical room undergoing surgery).

Particular embodiments described herein include a cartridge for use with a blood testing console. The cartridge may include a blood sample receiver configured to receive a blood sample to be tested. The cartridge may additionally include a hermetically sealed container of saline. The cartridge may be configured to mix a portion of the blood sample with the saline to achieve a desired dilution of a portion of the blood sample. To do so, the cartridge may include one or more fluid processing and testing paths. In various embodiments, the cartridge includes one or more valves and vents that enable control over the fluid flow through the fluid processing and testing paths. Namely, each fluid processing and testing path enables fluid flow into one or more measuring chambers that are each is configured to provide fluid through a valve to a corresponding mixing chamber. As such, a desired volume of blood or saline can be precisely measured by the measuring chamber and subsequently provided to the mixing chamber to achieve the desired dilution.

In various embodiments described herein, the cartridge is further configured to receive one or more reagents that are to be provided to the mixing solution within the mixing chamber. The reagent may be a reagent bead, and in various embodiments, the reagent is composed of a platelet activator. The cartridge may include a cartridge slider situated within the cartridge that is configured to receive the reagent, hold the reagent until a particular time, and provide the reagent to the appropriate mixing chamber. Additionally, in various embodiments described herein, the cartridge is configured to capture a measurement of the blood and saline mixture in the mixing chamber. Namely, the cartridge may include one or more cartridge electrodes, each positioned within the cartridge to capture an impedance measurement of the blood and saline mixture while the solution resides within the mixing chamber. In various embodiments, the measurement is captured after one or more reagents are provided to the mixing solution within the mixing chamber. As such, an identification of the platelet activity within the blood sample can be determined through the captured measurement.

Some or all of the embodiments described herein may provide one or more of the following advantages. First, some embodiments of the system are configured to be automated so that user interactions with the system are minimized. As a result, human resources can be diverted and utilized with greater efficiency. The reduction of user interactions can also reduce the chances for manual operator errors, such as measuring inaccuracies, reagent mixing errors, and the like. Accordingly, more accurate results may be attained in some circumstances.

Second, in some embodiments, the cartridge includes multiple fluid channels that are each individually controllable so that multiple different assays can be performed from a single supply of a blood sample. For example, each fluid channel between a measuring chamber and a mixing chamber includes a dedicated valve that is controllable by the analyzer console so that the blood flow is individually controllable. This feature enables the system to automatically perform sophisticated assay processes.

Third, in some embodiments, the cartridge includes chambers that are designed to accurately measure solution volumes, such that when blood and saline are mixed, a desired ratio of blood and saline can be accurately achieved. This enables testing reproducibility that is often difficult to achieve when manual intervention is required (e.g., pipetting).

Fourth, in some embodiments, the analyzer console can be configured to perform a number of quality-control operations/confirmations so as to ensure the blood test results are not compromised. For example, the analyzer console can be configured to verify the blood testing cartridge is heated to a target temperature (e.g., about 37° C.) prior to the blood sample being distributed to testing chambers of the cartridge. Because temperature of the blood sample can affect the coagulation characteristics in some circumstances, the accuracy of the results may be enhanced as a result of such temperature-control operations/confirmations.

Fifth, in particular embodiments of the cartridge device, the geometry of the fluid flow paths through the fluid channels of the cartridge are configured to reduce the potential for disturbing the fluid (e.g., causing bubble formation, etc.), and/or damaging the fluid, in a manner that may negatively impact the accuracy of the test results. Further advantages associated with the systems provided herein are also envisioned, as will be evident from the following disclosure.

The details of one or more embodiments of the invention are set forth in the accompanying drawings and the description below. Other features, objects, and advantages of the invention will be apparent from the description and drawings, and from the claims.

BRIEF DESCRIPTIONS OF THE DRAWINGS

The disclosed embodiments have other advantages and features which will be more readily apparent from the following detailed description of the invention and the appended claims, when taken in conjunction with the accompanying drawings, in which:

FIGS. 1A, 1B, 2, and 3 are perspective illustrations depicting the components and use of an example system, in accordance with an embodiment.

FIG. 6A is a view of the internal side of the left cover, in accordance with an embodiment.

FIG. 6B-6D depict perspective views of the left cover, in accordance with an embodiment.

FIG. 7A is a view of the internal side of the right cover, in accordance with an embodiment.

FIG. 7B is a view of the external side of the right cover, in accordance with an embodiment.

FIG. 7C depicts a top view of the right cover, in accordance with an embodiment.

FIG. 9A depicts a top down view of the cartridge electrodes within the cartridge body, in accordance with an embodiment.

FIG. 9B-9E each depicts a view of a cartridge electrode, in accordance with an embodiment.

FIG. 10A depicts a cartridge slider, in accordance with an embodiment.

FIG. 10B depicts a side view of the cartridge slider, in accordance with an embodiment.

Figure 11B:
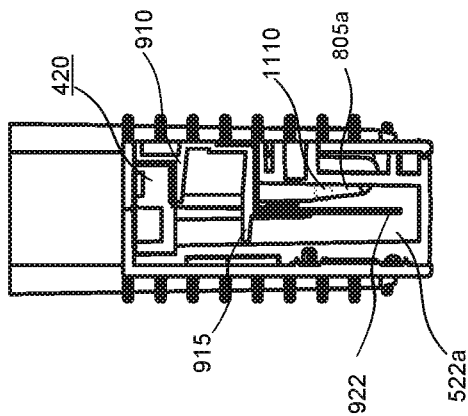
Figure 11A:
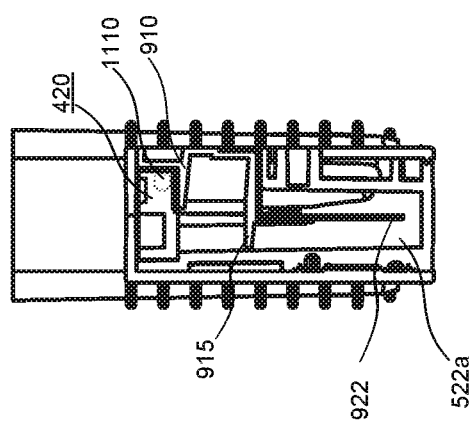

FIG. 11A-11B each illustrates a cutaway view of an assembled autoplatelet cartridge as a reagent bead enters into a mixing chamber, in accordance with an embodiment.

Figure 12A:
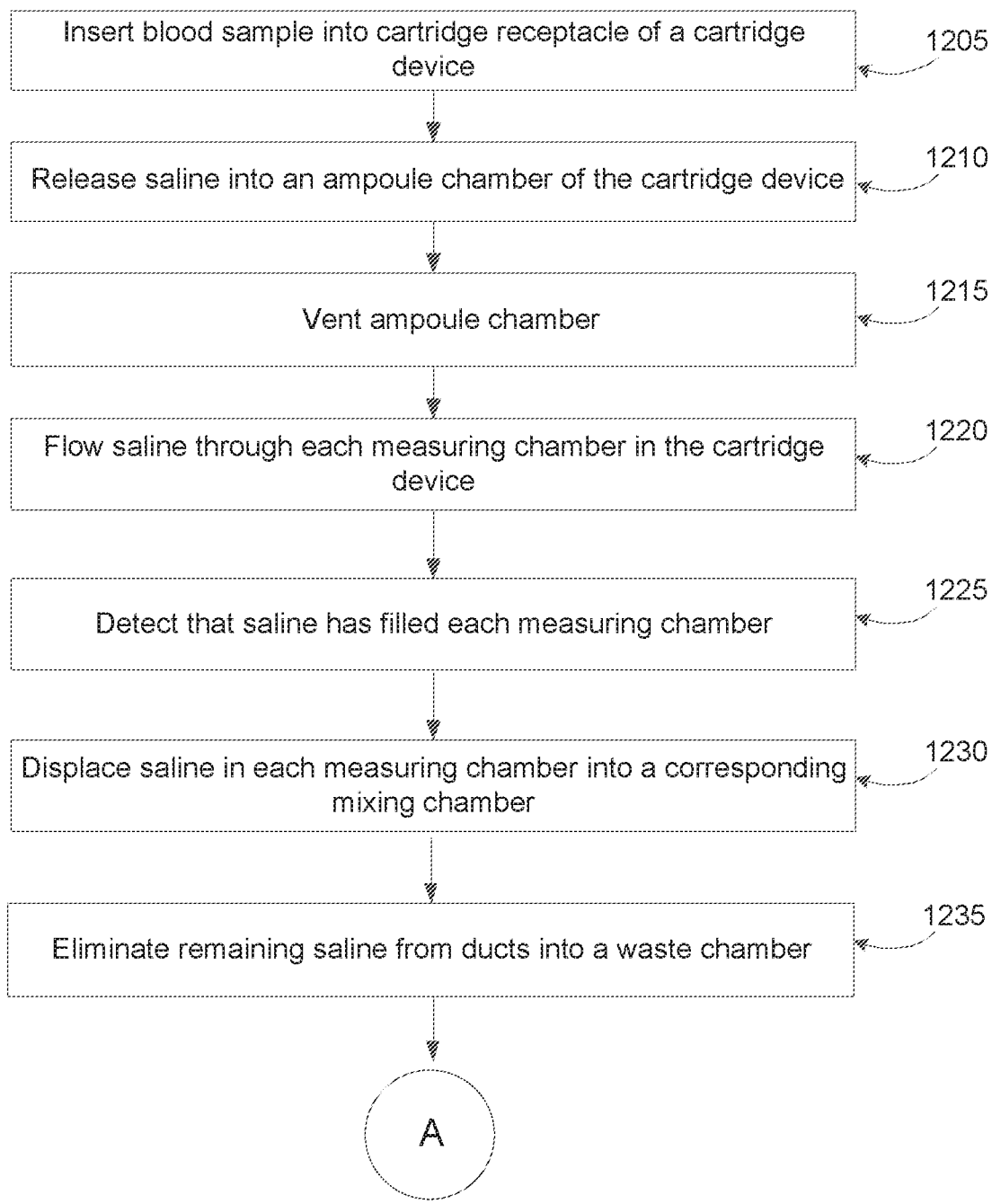
Figure 12B:
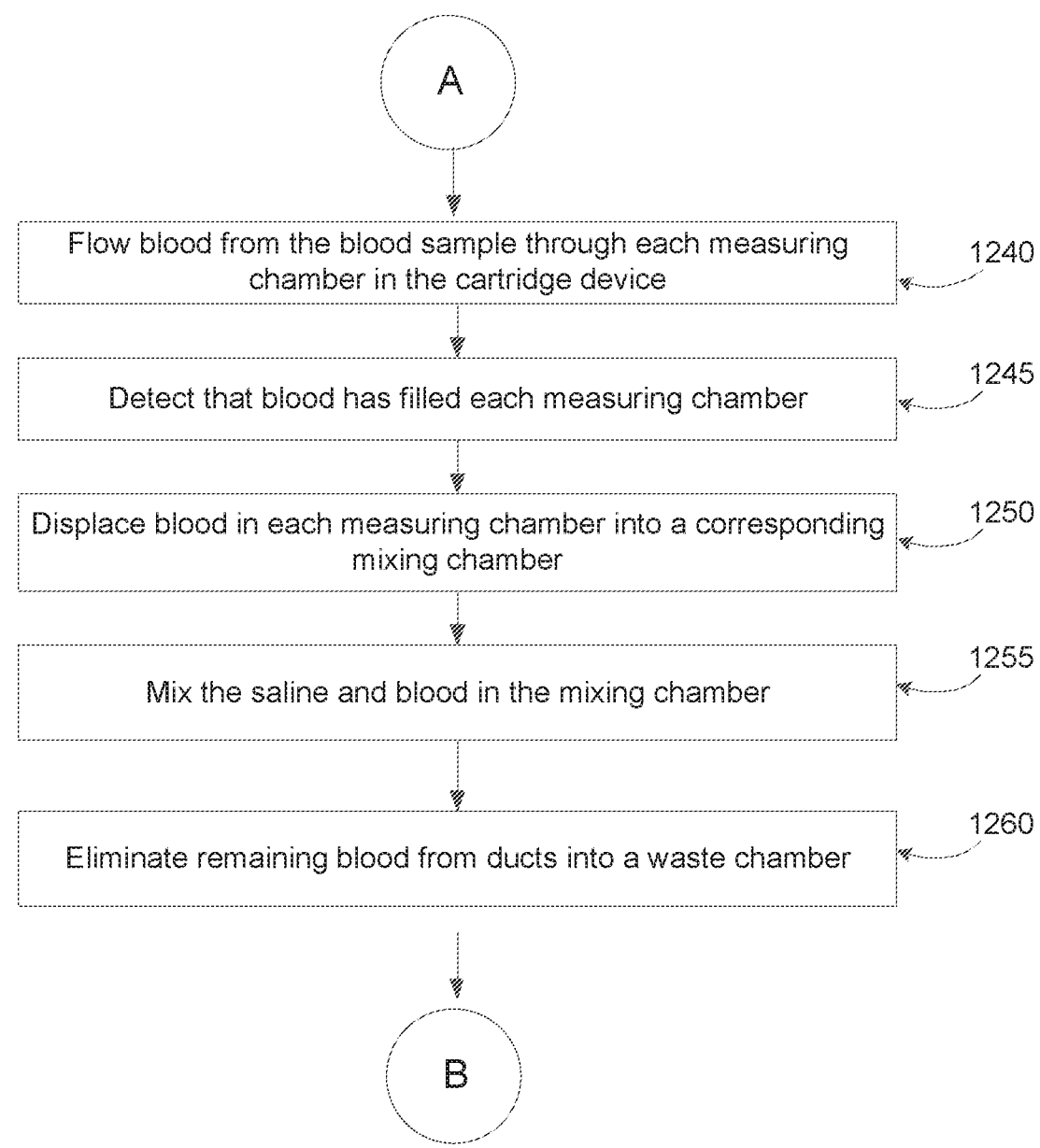
Figure 12C:
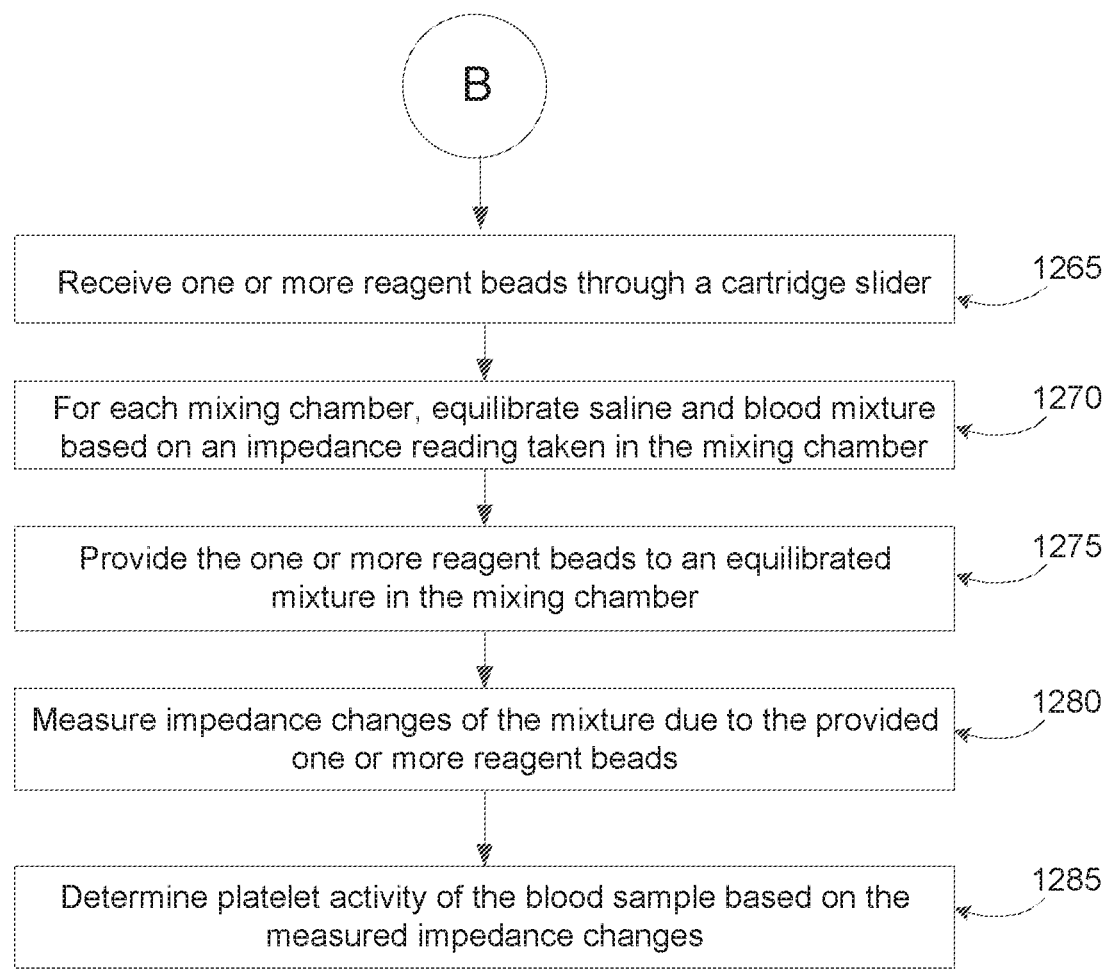

FIG. 12A-C illustrates a flow process of testing platelet behavior using the autoplatelet cartridge, in accordance with an embodiment.

Figure 13A:
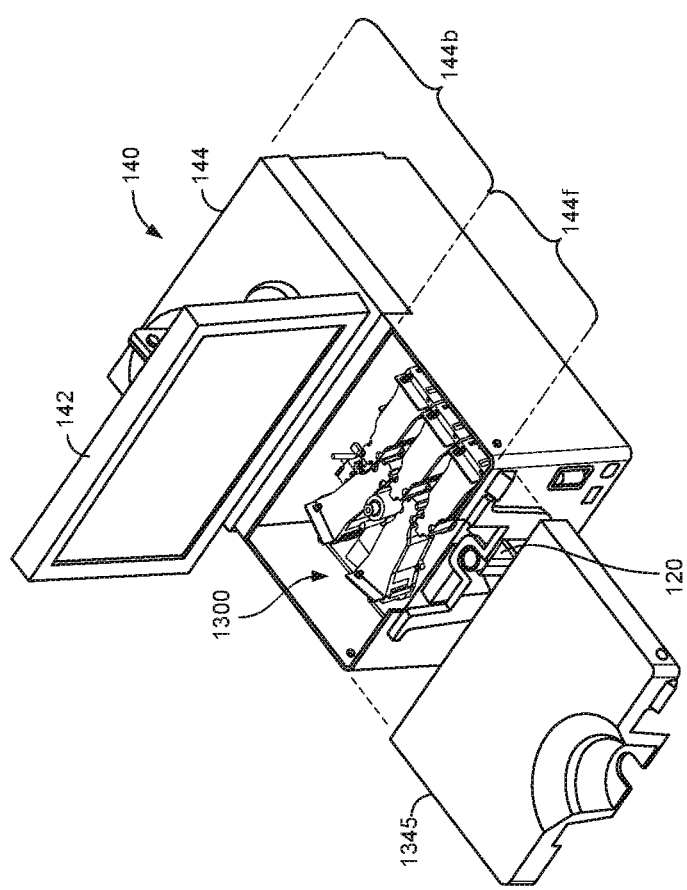
Figure 13B:
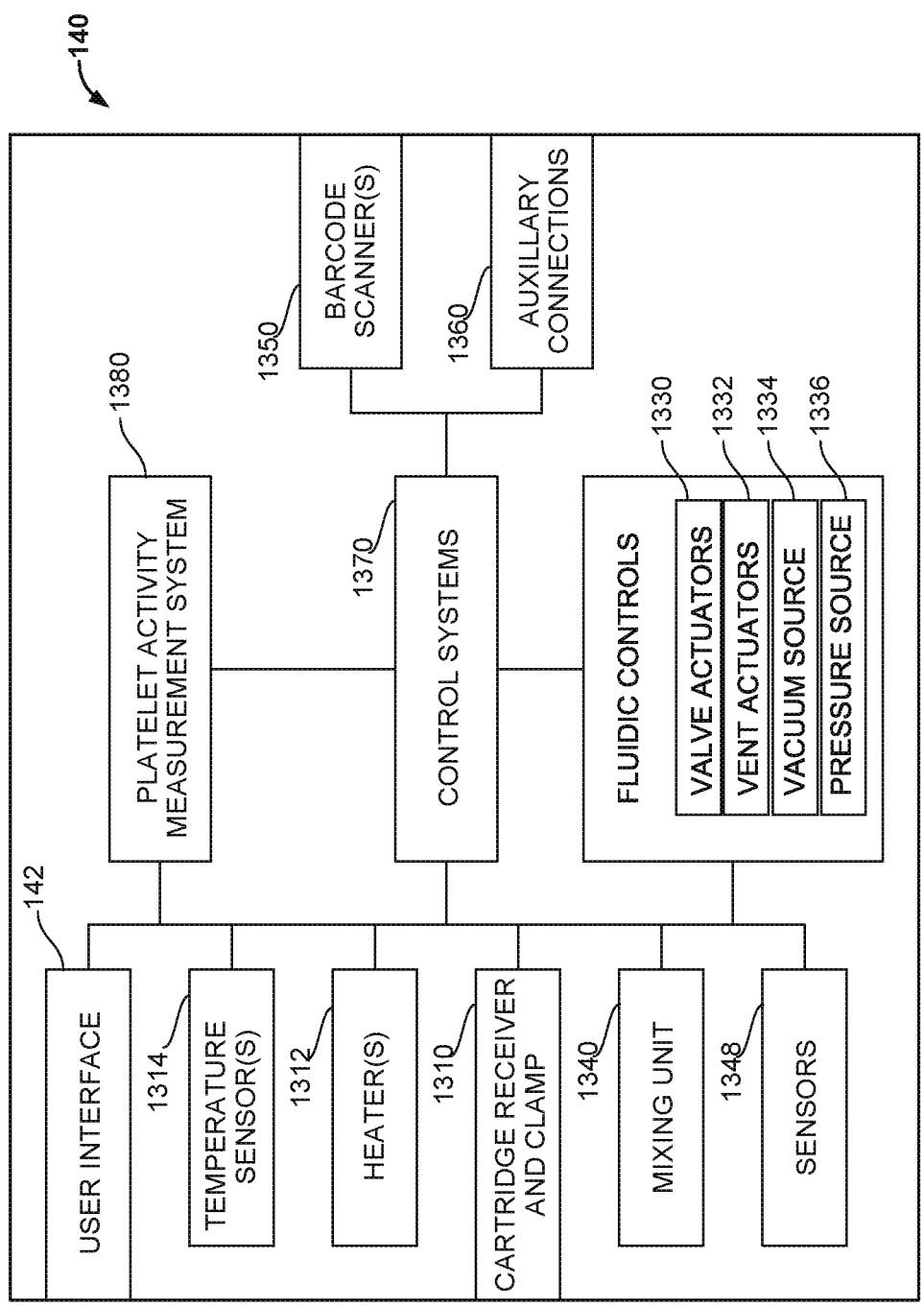

FIG. 13A-B illustrate an overview of the analyzer console, in accordance with an embodiment.

DETAILED DESCRIPTION

The figures and the following description relate to preferred embodiments by way of illustration only. It should be noted that from the following discussion, alternative embodiments of the structures disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system for purposes of illustration only. One skilled in the art will readily recognize from the following description that alternative embodiments of the structures illustrated herein may be employed without departing from the principles described herein.

The figures use like reference numerals to identify like elements. A letter after a reference numeral, such as "425a," indicates that the text refers specifically to the element having that particular reference numeral. A reference numeral in the text with multiple letters, such as "425a-c" refers to any individual or combination of the elements in the figures bearing that reference numeral.

Overview Configuration

Referring to FIGS. 1A-3, some embodiments of a blood testing system 100 include an analyzer console 140 and one or more autoplatelet cartridges 120 configured to releasably mate with analyzer console 140. In this embodiment, the blood testing system 100 is configured to determine a number of blood coagulation characteristics of a blood sample input into the autoplatelet cartridge 120. For example, the autoplatelet cartridge 120 can be configured as a single-use cartridge that includes a blood sample well 122 for mating with a blood sample reservoir 10 (e.g., a vacutainer sample tube supplied by Becton, Dickinson & Company of Franklin Lakes, N.J., or another blood reservoir structure). In some cases, an adapter may be used to couple other types of blood sample reservoirs 10 with the cartridge 120 (e.g., tubing may be used through which blood can be injected into the cartridge 120, and the like). The system 100 can be used as a whole blood coagulation analysis system that is particularly advantageous at a point-of-care site (e.g., in a surgical theater while a patient is undergoing or preparing for surgery, or the like). Additionally, system 100 can be used as a whole blood coagulation analysis system in a laboratory setting.

The analyzer console 140 includes a user interface 142 (with touchscreen display in this embodiment) and a main chassis 144. The user interface display 142 can be configured to output one or more graphical results 143 from the blood testing assays performed via the autoplatelet cartridge 120 and analyzer console 140 (e.g., one or more plots, such as those sometimes refer to as a TEMogram, numeric data or measurements, or a combination thereof). In some embodiments, the user interface display 142 is rigidly attached to the analyzer console 140. In particular embodiments, the user interface display 142 is pivotable and/or is otherwise positionally adjustable in relation to the main chassis 144. A main power switch 148 can be located at a convenient but protected location on the main chassis 144.

In the depicted embodiment, the touchscreen display 142 is configured to receive user input and to display output information to the user. For example, the user can enter information to the system 100 by making selections of various soft-buttons that may be displayed on the touchscreen display 142 at times during the beginning, middle, and end of the testing process. In some embodiments, other selections such as, but not limited to, soft keyboard entries can be provided via touchscreen display 142. In some embodiments, data entry can be performed additionally or alternatively by voice entry. In other embodiments, the user interface may include other peripheral devices can be included (e.g., a mouse, a keyboard, an additional display device, and the like) as part of the system 100. In some embodiments, a computer data network (e.g., intranet, internet, LAN, etc.) may be used to allow for remote devices to receive and/or input information from the system 100. For example, in some embodiments one or more remote displays can be utilized via network connections. In the depicted embodiment, the system 100 also includes an external barcode reader. The external barcode reader can facilitate convenient one-dimensional or two-dimensional barcode entry of data such as, but not limited to, blood sample data, user identification, patient identification, normal values, and the like. Alternatively or additionally, the system 100 can be equipped with a reader configured to read near-field communication tags, RFID tags, or the like.

In the depicted embodiment, the main chassis 144 houses various internal sub-systems (as described further below), includes various electronic connection receptacles (not shown), and includes a cartridge port 150. The various electronic connection receptacles can include network and device connectors such as, but not limited to, one or more USB ports, Ethernet ports (e.g., RJ45), VGA connectors, Sub-D9 connectors (RS232), and the like. Such connection receptacles can be located on the rear of the main chassis 144, or at other convenient locations on the main chassis 144. For example, in some embodiments one or more USB ports may be located on or near the front of the main chassis 144. A USB port, so located, may provide user convenience for recording data onto a memory stick, for example. In some embodiments, the system 100 is configured to operate using wireless communication modalities such as, but not limited to, Wi-Fi, Bluetooth, NFC, RF, IR, and the like.

Still referring to FIGS. 1A-3, the cartridge port 150 can be located at a readily accessible location on the main chassis 144. In the depicted embodiment, the cartridge port 150 is located on the front of the main chassis 144 so that it is conveniently accessible by a user in a point-of-care site. The cartridge port 150 defines an opening and internal space that is shaped complementarily to the outer dimensions of the autoplatelet cartridge 120. To insert the autoplatelet cartridge 120 into the cartridge port 150, the user can grasp the end of the autoplatelet cartridge 120 that includes the blood sample receiver 122 and slidingly insert the opposite end (leading end) into the cartridge port 150. The sliding insertion can continue until a hard-stop is reached that defines the fully inserted position. In the fully inserted position, a trailing end portion (including the blood sample receiver 122 in this embodiment) of the autoplatelet cartridge 120 remains exterior to the main chassis 144. The portion of the autoplatelet cartridge 120 that is received into the cartridge port 150 can include outer surface features (such as a tapered angle a rear end portion shown in FIG. 1B) that mate with at least one internal interface element inside the console 140 to ensure correct positioning of the autoplatelet cartridge 120. As such, at least the blood sample receiver 122 remains exterior to the main chassis 144 throughout the duration of the blood sample testing. In this configuration, the blood sample receiver 122 serves as a blood sample well that is accessible so that the blood sample reservoir 10 can be inserted into the receiver 122 while the autoplatelet cartridge 120 is mated with the console 140 in the fully inserted position. In some embodiments, the cartridge port 150 and the main chassis 144 are configured so that the exposed portion of the autoplatelet cartridge 120 is protected from inadvertent contact. As described further below, an internal sensor (e.g., a microswitch, an optical sensor, etc.) can detect when the autoplatelet cartridge 120 has been fully inserted into the main chassis 144.

When the analyzer console 140 has detected that the autoplatelet cartridge 120 has been fully inserted, in some embodiments the analyzer console 140 initiates one or more of the following actions. An internal cartridge clamping mechanism that includes positioning pins can be activated to accurately position and releasably retain the autoplatelet cartridge 120 in the fully inserted position. One or more cartridge heating elements can be activated to warm the cartridge 120. The temperature of the autoplatelet cartridge 120 can be monitored. A barcode on the leading end of the autoplatelet cartridge 120 can be read and the barcode data can be stored in memory of the analyzer console 140. One or more blood detection sensors can inspect the autoplatelet cartridge 120 for the presence of blood. The platelet activity measurement system can be engaged with the autoplatelet cartridge 120 to begin testing of the platelet. The cartridge 120 can be leak tested using vacuum or air pressure delivered by the analyzer console 140. For example, a pressure/vacuum decay test can be performed. In some embodiments, other actions can be additionally or alternatively activated when the analyzer console 140 has detected that the autoplatelet cartridge 120 has been fully inserted. After the completion of such actions, in some embodiments an indication of the results of the actions may be displayed on the touchscreen display 142 (e.g., pass or fail). If the analyzer console 140 determines that the actions were completed successfully, a prompt can be provided on the touchscreen display 142 that informs the user that the system 100 is ready to receive the blood sample reservoir 10. Further discussion regarding the analyzer console 140 of the system 100 is described below in reference to FIG. 13A-B.

Briefly, in some embodiments a user can operate the depicted system 100 embodiment as follows. First, the user can insert the autoplatelet cartridge 120 into the cartridge port 150 so that the autoplatelet cartridge 120 is placed into the fully inserted position. Completion of that step will automatically initiate a series of operations by the system 100 as described below. Upon successful completion of such operations, a notification that the blood collection tube 10 can be inserted into the sample well 122 will be displayed on the touchscreen display 142. After the user has mated the blood collection tube 10 into the sample well 122, the user initiates testing by pressing a "start" button (or the like) on the touchscreen display 142. At least the blood measuring, reagent mixing, and testing is performed automatically by the system 100 thereafter (e.g., without requiring manual intervention from the user in this embodiment). When the testing is completed, the results are displayed on the touchscreen display 142 in the form of qualitative graphical representations and quantitative parameters (e.g., as depicted in FIG. 1A). Also, when the testing is completed, the autoplatelet cartridge 120 can be removed from the analyzer console 140. The autoplatelet cartridge 120 may be reused or discarded.

Alternately, in some embodiments the blood collection tube 10 can be inserted into the sample well 122 of the autoplatelet cartridge 120 prior to insertion of the autoplatelet cartridge 120 into the cartridge port 150. In such circumstances, the blood from the collection tube 10 may not advance into the fluid channels of the autoplatelet cartridge 120 until after the analyzer console 140 acts upon the autoplatelet cartridge 120 (again, as described below). With the blood collection tube 10 being pre-coupled with the autoplatelet cartridge 120, the combination of the blood collection tube 10 and the autoplatelet cartridge 120 can then be inserted into the cartridge port 150.

Autoplatelet Cartridge Device

Figure 1:
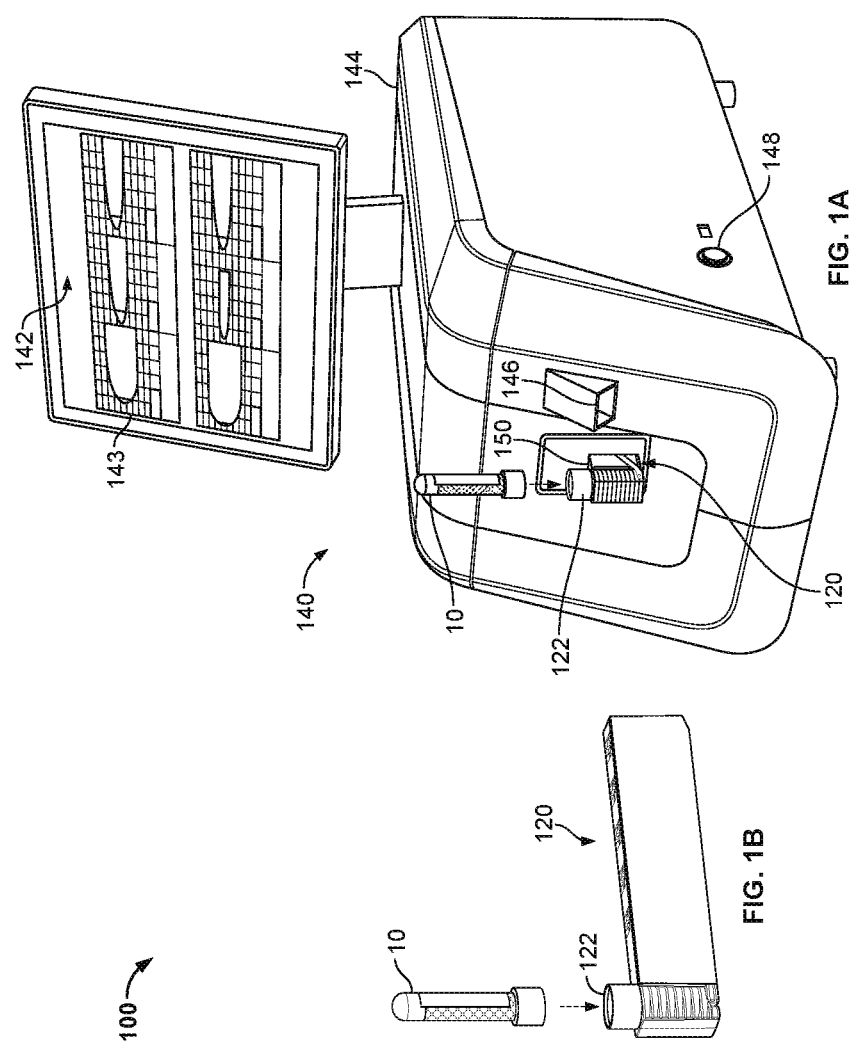
Figure 2:
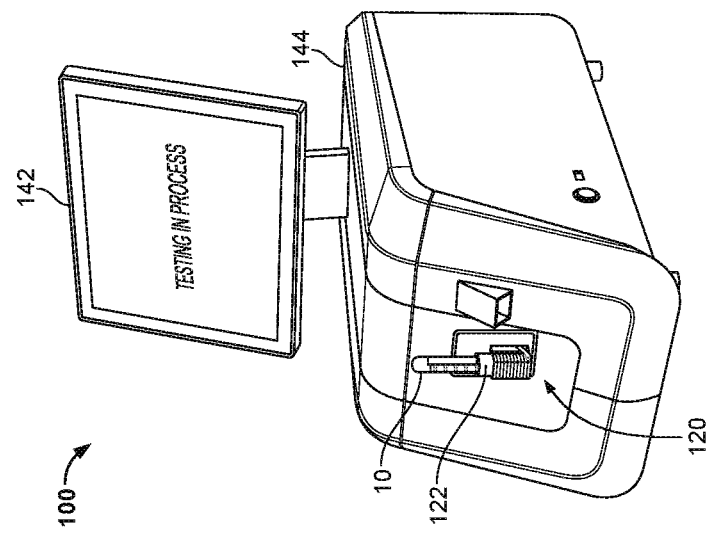
Figure 3:
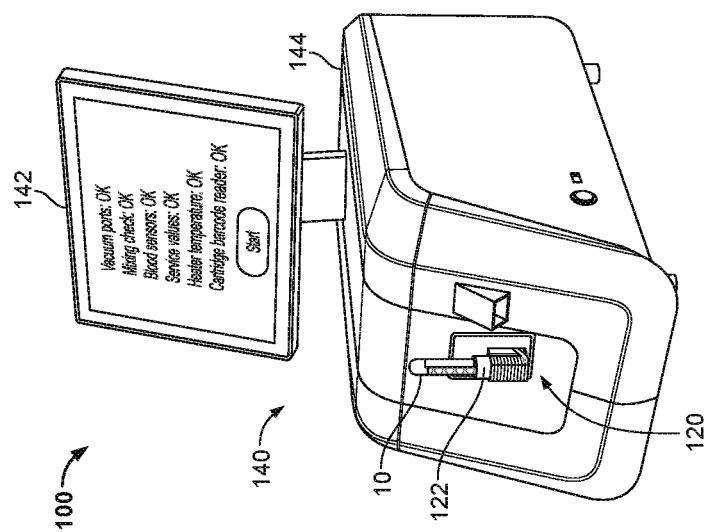
Figure 4:
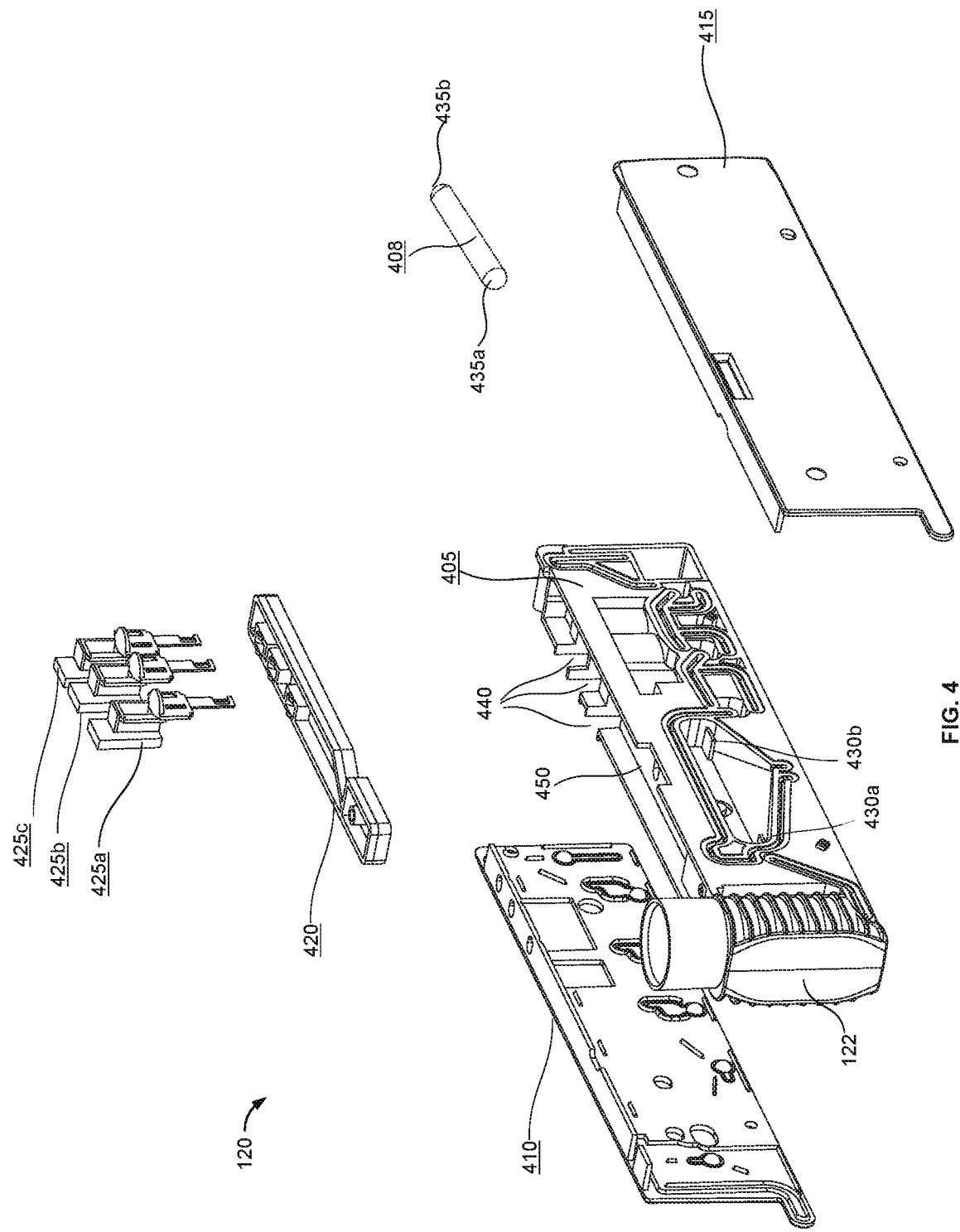
FIG. 4 is an exploded view of the example autoplatelet cartridge of the system of FIGS. 1A, 1B, 2, and 3, in accordance with an embodiment.

Reference is now made to FIG. 4, which depicts an exploded view of a sample autoplatelet cartridge 120 of the system 100 of FIGS. 1A, 1B, 2, and 3, in accordance with an embodiment. The autoplatelet cartridge 120 includes a cartridge body 405, a left cover 410, a right cover 415, an ampoule 408, a cartridge slider 420, and one or more cartridge electrodes 425a-c. In various embodiments, the autoplatelet cartridge 120 may further include one or more reagent beads. The reagent beads are included in the autoplatelet cartridge 120 for activating the platelets in a blood sample, thereby enabling the measurement of platelet activity in the blood sample.

The cartridge body 405 includes the aforementioned sample well 122 which is situated on one end of the cartridge body 405 as well as multiple ledges 430a-b that are each configured to be in contact with the ampoule 408 of the autoplatelet cartridge 120. The cartridge body 405 may further include a cavity 450 on a top surface of the cartridge body 405 as well as multiple slots 440 adjacent to the cavity 450. Each slot 440 may be located on the left wall of the cartridge body 405. Additional embodiments of the construction of an autoplatelet cartridge 120 are also envisioned. Each of the elements of the cartridge body 405 is further described below in regards to the other components of the autoplatelet cartridge 120.

The left cover 410 is affixed to left side of the cartridge body 405, and the right cover 415 is affixed to the right side of the cartridge body 405. As such, the left and right covers 410 and 415 enclose chambers and flow channels of the cartridge body 405 to define fluid flow paths as described further below.

The ampoule 408 of the autoplatelet cartridge 120 may include a first end 435a and a second end 435b. As depicted in FIG. 4, the ampoule 408 is cylindrical in shape with hemispherical ends 435a-b. In various embodiments, the ampoule 408 may take on any other number of form factors. In various embodiments, the ampoule 408 is a closed vessel such as a hermetically sealed container and stores a fluid. For example, the fluid may be a saline solution. More specifically, the fluid may be a normal saline solution. Additionally, the ampoule 408 may be constructed from an easily rupturable material such as glass or aluminum such that an external force imparted on a wall of the ampoule 408 would cause the ampoule 408 to rupture and release the stored fluid. In other embodiments, there is a valve or other release mechanism associated with the ampoule 408. In various embodiments, the ampoule 408 is configured to sit within a chamber of the cartridge body 405 when the autoplatelet cartridge 120 is fully assembled. For example, the first end 435a of the ampoule 408 sits in contact with a top surface of a first ledge 430a. Similarly, the second end 435b of the ampoule 408 sits in contact with a top surface of a second ledge 430b. The ampoule 408 can be geometrically configured such that when sitting in contact with the multiple ledges 430a-b within the chamber of the cartridge body 405, the ampoule 408 does not translationally displace relative to the cartridge body 405 due to being in contact with the ledges 430a-b and the walls of the chamber.

The cartridge electrodes 425a-c are each configured to determine platelet function (e.g., platelet aggregation) by measuring impedance and/or changes in impedance in a blood sample. When the autoplatelet cartridge 120 is assembled, each cartridge electrode 425a-c resides within a slot 440 in the cartridge body. As such, the cartridge electrode 425a-c can be used to take a measurement of a solution within the autoplatelet cartridge 120. In various embodiments, the cartridge electrodes 425a-c are geometrically designed to block off the slot 440 on the left wall of the cartridge body 405. Namely, the cartridge electrode 425a-c, when assembled with the cartridge body 405, prevents substances from entering into the cartridge body 405 through the slot 440.

The cartridge slider 420 is configured to slide within the cavity 450 of the cartridge body 405. When the autoplatelet cartridge 120 is assembled, the cartridge slider 420 is situated within the cavity 450 and above the cartridge electrodes 425a-c. Namely, the cartridge slider 420 longitudinally translates along the cavity 450 to achieve different positions. For example, in a first position, one or more reagent beads can be loaded into the autoplatelet cartridge 120. In a second position, one or more reagent beads can be dropped into a solution mixture such that an impedance measurement of the solution mixture can be taken by a cartridge electrode 425a-c. In various embodiments, the cartridge slider 420, when in the first position, is at a position in the cavity 450 that is most distal relative to the sample well 122. Therefore, the cartridge slider 420 is located more proximal to the sample well 122 in the second position relative to the first position.

Cartridge Body

Figure 5A:
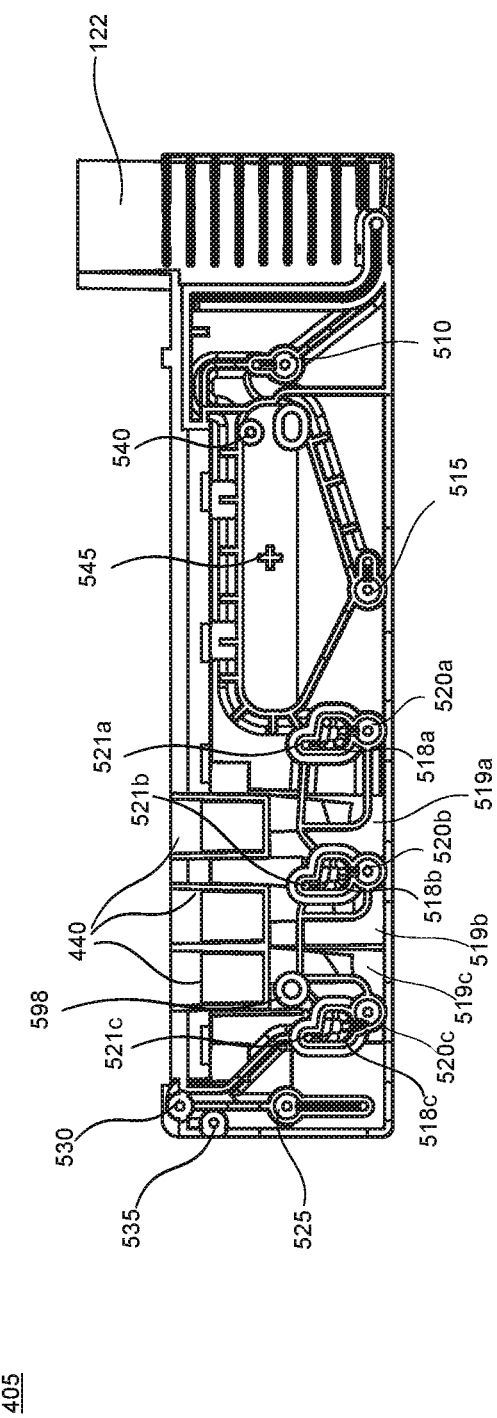
FIG. 5A is a left side view of the autoplatelet cartridge body, in accordance with an embodiment.
Figure 5B:
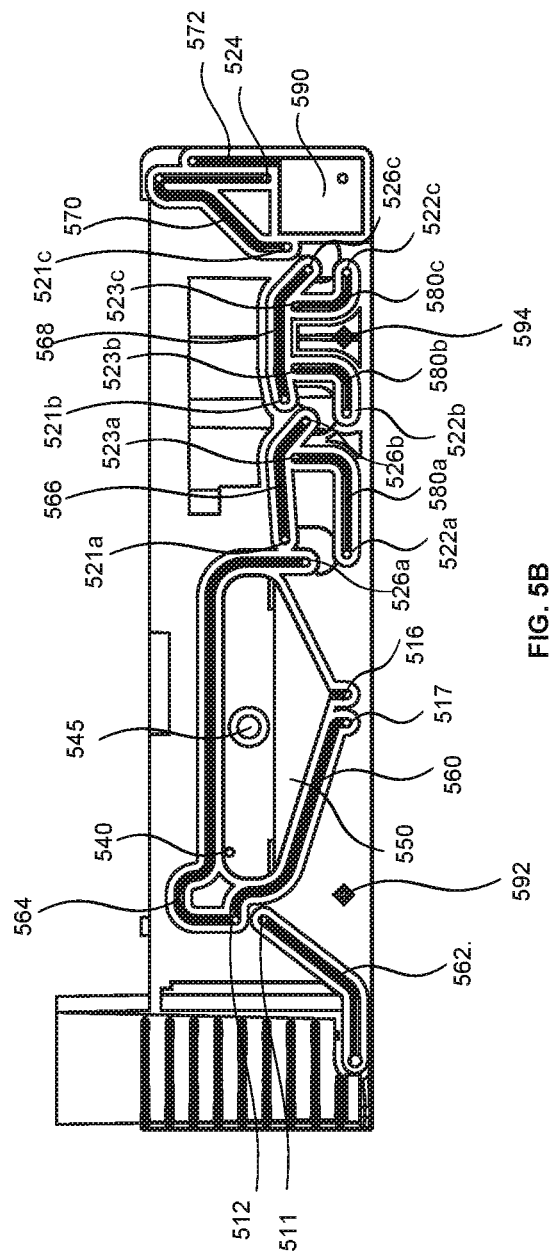
FIG. 5B is a right side view of the autoplatelet cartridge body, in accordance with an embodiment.

Reference is now made to FIG. 5A and FIG. 5B, which each depict a side view of the cartridge body 405, in accordance with an embodiment. Namely, FIG. 5A depicts a left side view of the cartridge body 405 whereas FIG. 5B depicts a right side view of the cartridge body 405. The elements of the cartridge body 405 will be discussed in reference to both the left side and right side view.

Referring to the left side view of the cartridge body 405 in FIG. 5A, the cartridge body 405 includes various valve seats 510, 515, 520a-c, and 525, an input pressure port 530, a vacuum pressure port 535, one or more measuring chambers 518a-c, one or more mixing chambers 519a-c, a vent port 540, a coupling point 598, and an ampoule access port 545. Referring to the right side view of the cartridge body 405 in FIG. 5B, the cartridge body 405 further includes various fluid channels 560, 562, 564, 566, 568, 570, 572, and 580a-c, an ampoule chamber 550, coupling points 592 and 594, and waste chamber 590. Additionally, the cartridge body 405 includes multiple ducts (511, 512, 516, 517, 521a-c, 522a-c, 523a-c, 524) that run transversely (e.g., from the left side to the right side and vice versa) through the cartridge body 405, the ducts fluidically connecting the fluid channels of the cartridge body 405.

In various embodiments, each of the valve seats 510, 515, 520a-c, and 525 in the cartridge body 405 are located on the left side of the cartridge body 405. A valve seat may be an indentation in the side of the cartridge body 405. Each valve seat 510, 515, 520a-c, and 525 is configured to receive and couple with a valve structure that is located on the left cover 410. When coupled with a valve structure, the valve seat 510, 515, 520a-c, and 525 is closed and prevents fluid flow through corresponding fluid channels. When not in contact with a reciprocal valve structure, the valve seat 510, 515, 520a-c, and 525 is open and allows fluid flow through the corresponding duct and fluid channel. Further discussion regarding the opening/closing of valve seats 510, 515, 520a-c, and 525 by a corresponding valve structure on the left cover 410 is further discussed in regards to FIG. 6. In various embodiments, the valve seats 510, 515, 520a-c, and 525 are interspersed within the path of the various fluid channels so that the fluid flow can be controlled by a valve structure according to predefined schemes.

Referring to the specific valve seats 510, 515, 520a-c, and 525 in the depicted embodiment in FIGS. 5A and 5B, valve seat 510 controls the fluid flow that originates from a blood sample reservoir 10 located in the blood sample receiver 122. Namely, the blood sample flows through fluid channel 562 to duct 511 (see FIG. 5B) that is connected to valve seat 510 (see FIG. 5A). Therefore, when valve seat 510 is open, blood can flow from fluid channel 562, through duct 511, through open valve seat 510, through duct 512, and into fluid channel 564. Valve seat 515 controls fluid flow between ampoule chamber 550 and fluid channel 560. Specifically, when valve seat 515 is open, fluid (e.g., saline) from the ampoule chamber 550 can flow through duct 516, through open valve seat 515, through duct 517, and into fluid channel 560. Valve seat 520a-c controls the fluid flow between the respective measuring chamber 518a-c and fluid channel 580a-c. Specifically, when valve seat 520a is open, fluid from the measuring chamber 518a flows through duct 522a into the corresponding fluid channel 580a. Similarly, when valve seat 520b is open, fluid from the measuring chamber 518b flows through duct 522b into the corresponding fluid channel 580b. Also, when valve seat 520c is open, fluid from the measuring chamber 518c flows through duct 522c into the corresponding fluid channel 580c. Fluid in fluid channel 580a-c can flow through a corresponding duct 523a-c that is fluidically connected to each mixing chamber 519a-c. Valve seat 525 controls fluid flow from fluid channel 570 to waste chamber 590. Specifically, when valve seat 525 is open, fluid flows from the fluid channel 570, through duct 524, through open valve seat 525 and into waste chamber 590.

The cartridge body 405 contains one or more measuring chambers 518a-c. As depicted in FIG. 5A, there are three total measuring chambers 518a-c; however, in other embodiments there may be additional or fewer measuring chambers 518a-c. Each measuring chamber 518a-c may have a defined volume (e.g., 150 µL), such that when the measuring chamber 518a-c is full of a particular fluid, the volume of that fluid is precise or nearly precise to the defined volume. Each measuring chamber 518a-c is in fluid connection with a fluid channel. For example, measuring chamber 518a receives fluid from fluid channel 564 through a duct 526a. Measuring chamber 518b receives fluid from fluid channel 566 through a duct 526b. Measuring chamber 518c receives fluid from fluid channel 568 through a duct 526c.

In various embodiments, the fluid in a measuring chamber 518a-c can exit in one of two different ways. In one way, as previously described, the fluid output of each measuring chamber 518a-c is controlled by a valve seat 520a-c that outputs through duct 522 and into corresponding fluid channel 580. In a second way, the fluid output of each measuring chamber 518a-c occurs through a corresponding duct 521a-c. Each duct 521a-c is fluidically connected with a corresponding fluid channel 566, 568, and 570. In various embodiments, each duct 521a-c is located at the top of each measuring chamber 518a-c such that fluid flows into the duct if the measuring chamber 518a-c is at maximum capacity. Therefore, altogether, the measuring chambers 518a-c are fluidically connected to one another through fluid channels 566 and 568. Namely, the fluid from measuring chamber 518a can flow through fluid channel 566 into measuring chamber 518b which can subsequently flow through fluid channel 568 into measuring chamber 518c.

The cartridge body 405 also contains one or more mixing chambers 519a-c, where each mixing chamber 519a-c is fluidically connected to a previously described measuring chamber 518a-c. In various embodiments, a mixing chamber 519a-c receives and mixes two different fluids (e.g., saline and blood). The mixing chamber 519a-c may each include a mixing device (e.g., a magnetic stir bar). In one scenario, the mixing chambers 519a-c may each extend to the bottom of the cartridge body 405 such that a magnetic field can be applied by the analyzer console 140 to the bottom of the cartridge body 405 to actuate the mixing devices located within the mixing chamber 519a-c.

In various embodiments, the volume of the mixing chamber 519a-c is at least twice the volume of the measuring chamber 518a-c. This enables the mixing of equal volumes of two different fluids that are each initially measured in the measuring chamber 518a-c. Additionally, each mixing chamber 519a-c is configured to receive a cartridge electrode 425a-c such that at least a portion of each cartridge electrode 425a-c can be exposed to a mixing solution within a mixing chamber 519a-c.

Input pressure port 530 is a pressure application port where a source of pressure can be applied. Namely, when a positive source of pressure is applied at input pressure port 530, and when the vents and valves of the cartridge 120 are in the proper configuration, fluid can be forced to flow from the measuring chambers 518a-c into the mixing chambers 519a-c. As depicted in FIGS. 5A and 5B, the input pressure port 530 is in fluid communication with the fluid channel 570. The process of applying a positive pressure at the input pressure port 530 is further described below.

Vacuum pressure port 535 is a vacuum application port where a negative source of pressure can be applied. Namely, when a source of vacuum is applied at the vacuum pressure port 535, and when the vents and valves of the autoplatelet cartridge 120 are in the proper configuration, fluid can be drawn into each of the measuring chambers 518a-c as described above. As depicted in FIGS. 5A and 5B, the vacuum pressure port 535 is in fluid communication with the waste chamber 590 through fluid channel 572. The process of applying the negative pressure at the vacuum pressure port 535 is further described below.

The cartridge body 405 may also include an ampoule chamber 550 that is configured to house the ampoule 408 that includes a fluid (e.g., saline). As previously described, the ampoule rests on the ledges 430a-b within the ampoule chamber 550. The cartridge body 405 also includes an ampoule access port 545. In various embodiments, the ampoule 408 within the ampoule chamber 550 receives an external force through the ampoule access port 545. The external force may comprise a physical force input provided by a structure that passes through the ampoule access port 545. Alternatively or in addition, the external force may comprise non-contact force such as the provided by an ultrasound application. This may cause the ampoule 408 to release the fluid within the ampoule 408 into the ampoule chamber 550. As such, the fluid in the ampoule chamber 550 can exit through duct 516, through open valve seat 515, and through duct 517 into fluid channel 560. In various embodiments, the cartridge body 405 may include a vent port 540 within the ampoule chamber 550. The opening and closing of the vent port 540 can be controlled by the analyzer console 140 in order to ensure that fluid can appropriately flow through the fluid channels. Namely, when fluid is exiting the ampoule chamber 550 through open vent 515, the vent port 540 is opened to provide proper venting into the ampoule chamber 550.

The cartridge body 405 also includes coupling points 592 and 594 on the right side of the cartridge body 405 that couple with the right cover 415. Similarly, the cartridge body 405 may include coupling point 598 on the left side of the cartridge body 405 that couples with the left cover 410.

Cartridge Covers

FIG. 6A is a view of the internal side of the left cover 410, in accordance with an embodiment. The left cover includes multiple valve structures 605a-f, vent opening 615, one or more divots 612a-c, ampoule opening 635, and one or more pressure openings 620. Further reference will be made to FIGS. 6B-6D which depict perspective views of the left cover 410, in accordance with an embodiment. More specifically, FIG. 6B illustrates a view of section H-H as depicted in FIG. 6A. FIG. 6C depicts detail J of FIG. 6B. FIG. 6D depicts a top down view of the left cover 410.

The left cover 410 includes a vent opening 615 that substantially aligns with the vent port 540 on the left side of the cartridge body 405. As such, the vent port 540 is open to the external environment which enables it to appropriately vent the ampoule chamber 550. The pressure openings 620 on the left cover 410 are positioned to substantially align with input pressure port 530 and vacuum pressure port 535, respectively. Therefore, the analyzer console 140 can access each port through the pressure openings 620 and apply a positive or negative pressure as needed. Similarly, the ampoule opening 635 is substantially aligned with the ampoule access port 545 on the left side of the cartridge body 405. Therefore, the analyzer console 140 can provide an external force through the ampoule opening 635 in order to release the fluid of the ampoule 408 within the cartridge body 405.

The left cover 410 also includes one or more divots 612a-c that are located on the underside of an overhang of the left cover 410. Referring to FIG. 6B, the overhang 630 of the left cover 410 extends perpendicular from the vertical portion of the left cover 410. Each of the divots 612a-c may be configured to be in contact with one or more structures on the cartridge slider 420 that is situated underneath the overhang 630 of the left cover 410. As an example, a divot 612a-c is an indentation in the overhang 630 of the left cover 410. The interface between the divot 612a-c and the structures of the cartridge slider 420 is described in further detail below in regards to FIG. 10.

The multiple valve structures 605a-f are located at various locations of the left cover 410 to correspond to the locations of the valve seats 510, 515, 520, and 525 on the left side of the cartridge body 405. As previously stated, each valve structure 605a-f is configured to contact or couple with a corresponding valve seat 510, 515, 520a-c, and 525. Therefore, when a valve structure 605a-f is in contact with a corresponding valve seat 510, 515, 520a-c, and 525, fluid flow through corresponding fluid channels is blocked.

Reference is now made to FIG. 6C that provides, in more detail, the structure of a valve structure 605d. In various embodiments, each valve structure 605a-f includes an elastomeric member 610 that is responsible for contacting a corresponding valve seat 510, 515, 520a-c, and 525. As depicted in FIG. 6C, the elastomeric membrane 610 is a hemispheric structure.

In various embodiments, the elastomeric member 610 of each valve structure 605a-f is deformable upon application of pressure on the external side of the left cover 410. Application of external pressure on the elastomeric member 610 of the valve structure 605a-f causes the elastomeric member 610 to deform inward (e.g., in FIG. 6C, towards the left), thereby contacting a corresponding valve seat 510, 515, 520, and 525 and fluidically sealing a corresponding fluid channel.

In various embodiments, the application of external pressure on a valve structure 605a-f can be actuated by the analyzer console 140. For example, the analyzer console 140 may utilize valve actuators that include a coupled pin. The coupled pin can extend to make contact with and to distend elastomeric material 610 of valve structures 605a-f such that the elastomeric material 610 makes contact with a valve seat 510, 515, 520a-c, and 525 within the cartridge body 405. In other embodiments, a valve actuator may comprise a solenoid that includes internal springs that cause the valve actuators to be normally extended. Accordingly, such normally closed solenoids will close the valve structures/seats of the cartridge body 405 as a default configuration.

Referring now to FIG. 6D, the overhang 630 of the left cover 410 may include three overhang openings 625*a-c*. Each overhang opening 625*a-c* is configured to receive reagent beads for the testing of platelet activity. For example, the overhang opening 625*a-c* may be circular or ovoid in shape, the overhang opening 625*a-c* being larger than the diameter of a reagent bead, such that the reagent bead can be provided to the underlying cartridge slider 420 and into the cartridge body 405. Additionally, the overhang 630 includes an indentation 640. The indentation 640, in part, allows access to the cartridge slider 420 that sits underneath the overhang 630.

Reference is now made to FIG. 7A, which depicts a view of the internal side of the right cover 415, in accordance with an embodiment. FIG. 7B is a view of the external side of the right cover 415, in accordance with an embodiment. The right cover 415 includes a slider access port 710 and one or more elevated structures 705 on the internal side of the right cover 415. Additionally, the right cover 415 includes one or more fluid detection locations 730*a-b* as well as one or more coupling points 720 and 725.

The slider access port 710 enables access to the side of the cartridge slider 420. In various embodiments, the slider access port 710 is rectangular in shape, thereby allowing access to a horizontal portion of the cartridge slider 420. The right cover 415 may also include one or more coupling points 720 and 725 that are positioned to substantially align with coupling points 592 and 594 of the right side of the cartridge body 405. In various embodiments, the right cover 415 also includes one or more elevated structures 705 that may be designed to correspond to the various fluid channels 560, 562, 564, 566, 568, 570, 572, and 580*a-c* of the cartridge body 405. Namely, when fluid is flowing through the fluid channels, the elevated structures 705 of the right cover 415 assist in preventing fluid from escaping the fluid channels into other portions of the cartridge body 405.

The fluid detection locations 730*a-b* are positioned on the right cover 415 to detect the presence of fluid in particular locations within the cartridge body 405. As will be described further below, the fluid detection location 730*a-b* are designated locations on the cartridge body 405 at which sensors of the analyzer console 140 interface with the autoplatelet cartridge 120. In some embodiments, the sensors applied to the fluid detection location 730*a-b* are optical sensors, such as IR (infrared) sensors. In some embodiments, the fluid detection locations 730*a-b* are polished areas that have enhanced transparency and optical clarity. As such, the right cover 415 is configured so that the optical sensors of the analyzer console 140 can readily detect the presence or absence of fluid at the fluid detection locations 730*a-b*. As an example, fluid detection location 730*a* detects fluid in fluid channel 564 whereas fluid detection location 730*b* detects fluid in fluid channel 570 before the fluid enters into waste chamber 590.

Referring now to FIG. 7C, it depicts a top view of the right cover 415, in accordance with an embodiment. The right cover 415 may include an overhang 715 (similar to overhang 630 on the left cover 410) that is located at the top of the right cover 415 and extends perpendicular to the vertical portion of the right cover 415. Additionally, the overhang 715 may include an indentation 740 that is designed to align with the indentation 640 of the overhang 630 of the left cover 415. Therefore, when taken together, the two indentations 640 and 740 form an opening that enables access to the cartridge slider 420 located underneath the overhangs 630 and 715 of the left cover 410 and right cover 415, respectively.

Mixing Chamber of the Cartridge Body

Figure 8A:
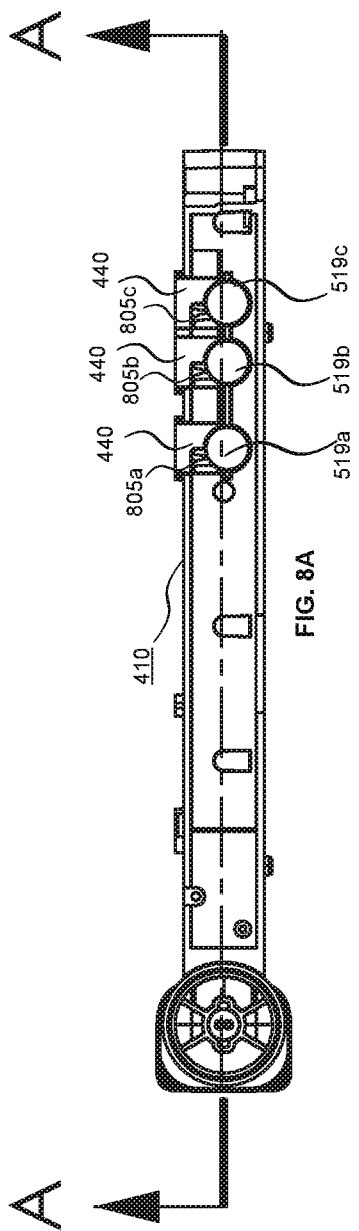
FIG. 8A depicts a top down view of the cartridge body, in accordance with an embodiment.

FIG. 8A depicts a top down view of the cartridge body 405, in accordance with an embodiment. As previously described, the cartridge body 405 includes multiple openings 440 that are located along the left side of the cartridge body 405 and above the mixing chambers 519*a-c*. Additionally, the cartridge body 405 includes bead drop inlets 805*a-c* located within the mixing chambers 519*a-c*.

In various embodiments, the multiple slots 440 along the side of the cartridge body 405 extend from the top of the cartridge body 405 down a certain distance along the cartridge body 405. In various embodiments, the multiple slots 440 extend downward a distance that is less than half of the height of the cartridge body 405. As depicted in FIG. 8A, mixing chambers 519*a-c* are cylindrically shaped. As previously described, each mixing chamber 519*a-c* may include a mixing device (e.g., a magnetic stirrer) that facilitates the mixing of fluid within the mixing chamber 519*a-c*. In various embodiments, the bead drop inlets 805*a-c* are located along the cartridge body 405 such that a reagent bead can be provided through the bead drop inlet 805*a-c* to a mixing chamber 519*a-c*. As an example, the bead drop inlets 805*a-c* are substantially aligned with the overhang openings 625*a-c* of the left cover 410. Thus, a reagent bead provided to the autoplatelet cartridge 120 through the overhang openings 625*a-c* can directly drop downward through the bead drop inlets 805*a-c* into a mixing chamber 519*a-c*, provided that the cartridge slider 420 is in the correct position.

Figure 8B:
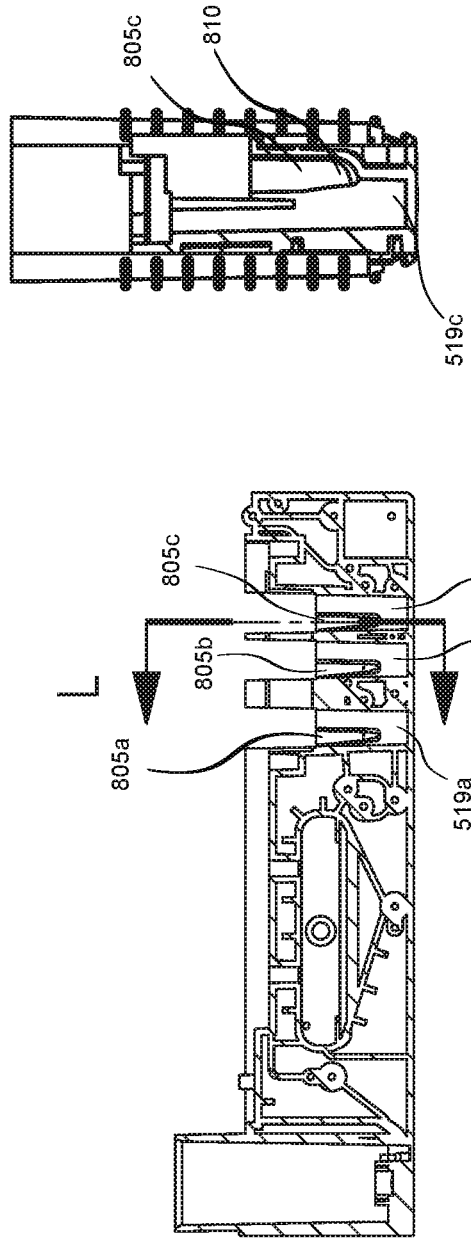
FIG. 8B depicts a cutaway of the cartridge body including the bead drop inlet, in accordance with an embodiment.

Reference is now made to FIG. 8B, which depicts a cutaway of the cartridge body 405 including the bead drop inlet 805*a-c*, in accordance with an embodiment. In various embodiments, each mixing chamber 519*a-c* includes a bead drop inlet 805*a-c* that extends vertically to the slot 440 located above the mixing chamber 519*a-c*. The bead drop inlet 805*a-c* may be located on one side of the mixing chamber 519*a-c*; namely, the bead drop inlet 805*a-c* is depicted to be on the left side of each mixing chamber 519*a-c* in FIG. 8B. In various embodiments, the height of each mixing chamber 519*a-c* is designed such that the mixing fluid (e.g., 300 μL total) in the mixing chamber 519*a-c* does not escape through the slots 440 along the left side of the cartridge body 405.

Figure 8C:
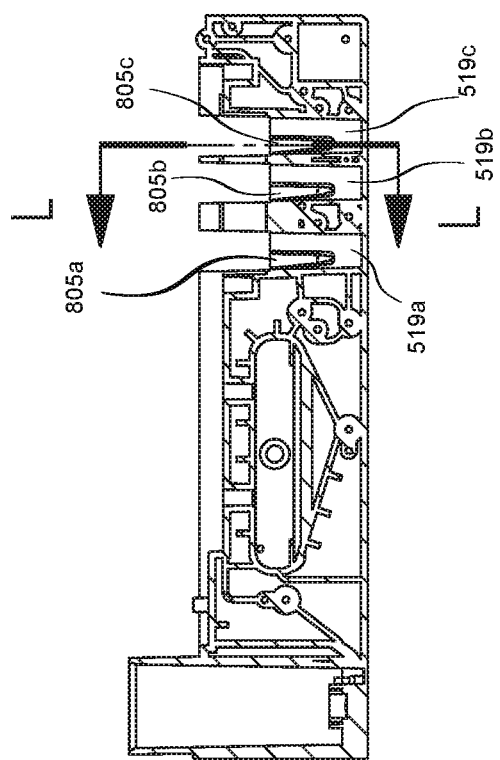
FIG. 8C depicts a side cutaway of the cartridge body that illustrates the bead drop inlet in relation to a mixing chamber, in accordance with an embodiment.

Reference is now made to FIG. 8C, which depicts a side cutaway of the cartridge body 405 that illustrates the bead drop inlet 805*c* in relation to a mixing chamber 519*c*, in accordance with an embodiment. In various embodiments, the bead drop inlet 805*a-c* is structurally configured to facilitate the entry of a reagent bead into a mixing chamber 519*a-c*. For example, as depicted in FIG. 8C, the bottom 810 of the bead drop inlet 805*c* may be structurally curved such that the reagent bead is directed away from the side of the cartridge body 405 into the mixing fluid in the mixing chamber 519*c*.

Cartridge Electrode and Cartridge Slider

Reference is now made to FIG. 9A, which depicts a top down view of the cartridge electrodes 425*a-c* within the cartridge body 405, in accordance with an embodiment. Namely, each cartridge electrode 425*a-c* is positioned within a slot 440 and extends into a mixing chamber 519*a-c*. In various embodiments, when cartridge electrodes 425*a-c* are inserted into the cartridge body 405, the cartridge electrodes 425*a-c* sit flush with the left cover 410 of the autoplatelet cartridge 120. The left side of the auotplatelet cartridge 120 does not have any protrusions, thereby facilitating the process of inserting the autoplatelet cartridge 120 into the analyzer console 140.

The cartridge body 405 may further include multiple loading structures 940a-c, each loading structure 940a-c adjacent to a corresponding cartridge electrode 425a-c. As depicted in FIG. 9A, each loading structure 940a-c is to the right of a cartridge electrode 425a-c. The loading structures 940a-c are positioned such that each loading structure 940a-c can receive a reagent bead when the reagent bead is first loaded into the assembled autoplatelet cartridge 120. Each loading structure 940a-c prevents the bead from entering into the mixing chamber 519a-c.

Reference is now made to FIG. 9B-9E, which each depicts a view of a cartridge electrode 425a-c, in accordance with an embodiment. The cartridge electrode 425a-c includes a platform 910, a sealing structure 915, a sealing face 918, an extension structure 922, one or more electrode wires 920a-b, and one or more contact pads 925a-b. Further description regarding the design of cartridge electrodes 425a-c for measuring platelet activity is described in U.S. application Ser. No. 14/864,634 which is hereby incorporated in its entirety by reference.

The platform 910 of the cartridge electrode 425a-c serves as a structure that holds a reagent bead prior to being provided to the mixing chamber 519a-c. Namely, the reagent bead sits in contact and on top of the platform 910. In various embodiments, the platform is a horizontal structure and is formed from an elastomeric material. The elastomeric material may be an insulating material. As such, the platform 905 insulates a reagent bead from temperature differences within the cartridge body 405. As an example, the reagent bead may be held on the platform 910 while the solution in the mixing chamber 519a-c is mixed and equilibrated (e.g., to 37° C.). Therefore, the platform 905 insulates the reagent bead from the heat that may arise from the mixing solution that may otherwise adversely affect the activity of the reagent bead.

In various embodiments, when the cartridge electrode 425a-c is within the cartridge body 405, the platform 910 is located immediately adjacent to a corresponding loading structure 940a-c. As such, the platform 910 can receive a reagent bead from the loading structure 940a-c and subsequently provide the reagent bead to the mixing chamber 519a-c. The process of loading a reagent bead into the autoplatelet cartridge 120 is discussed in further detail below.

Each cartridge electrode 425a-c may also include a sealing structure 915 that is configured to prevent mixing fluid from leaving the mixing chamber 519a-c. Namely, the sealing structure 915 serves as a structural barrier located above the mixing chamber 519a-c. In various embodiments, the sealing structure 915 is designed to correspond to a structure of the mixing chamber 519a-c. For example, as previously stated, the mixing chamber 519a-c may be cylindrical in shape. Therefore, the sealing structure 915 may be correspondingly designed with a circular or hemispherical seal to prevent mixing fluid from leaving the mixing chamber 519a-c. For example, the sealing structure 915 includes a sealing face 918 that is configured to sit in contact with the walls of the mixing chamber 519a-c. The sealing face 918 may be composed of a substance that further prevents fluid from escaping the mixing chamber 519a-c. This includes amounts of evaporated fluid from the mixing fluid that may alter the humidity of the microenvironment around the platform 910 of the cartridge electrode 425a-c (e.g., where the reagent bead resides). As an example, the sealing face 918 may be coated with a hydrophobic surface coating. As another example, the sealing face 918 may be a rubberized O-ring that enables a strong seal between the sealing structure 915 and the walls of the mixing chamber 519a-c.

The extension structure 922 of the cartridge electrode 425a-c extends into the mixing fluid solution within the mixing chamber 519a-c to enable one or more measurements to be taken by the electrode wires 920a-b. The extension structure 922 vertically extends downward away from the body of the cartridge electrode 425a-c and guides the electrode wires 920a-b by providing structural integrity to the electrode wires 920a-b. As depicted in FIG. 9B, the extension structure 922 includes a cavity 924 such that a portion of the electrode wires 920a-b can be exposed to the mixing fluid solution without contacting the extension structure 922. The extension structure 922 couples with the electrode wires 920a-b on both sides of the cavity 924.

The electrode wires 920a-b can be composed of palladium-, silver-, or gold-coated copper or can be pure, uncoated palladium, silver, gold, or copper. Using palladium-coated copper, for example, can substantially reduce the price of manufacture of the electrode assembly. The electrode wires 920a-b can be attached to the extension structure 922 by glue, adhesive tape, heat staking, welding (e.g., ultrasonic welding), or any other suitable attachment method that does not damage the electrode wires 920a-b.

In various embodiments, the electrode wires 920a-b are positioned perpendicular to a flow of the mixing solution within the mixing chamber 519a-c. As such, the electrode wires 920a-b can measure impedance or changes in impedance as the fluid flows perpendicular to the electrode wires 920a-b. More specifically, as platelet aggregation occurs on the exposed electrode wires 920a-b, the impedance and change in impedance can be measured to determine the level of platelet aggregation and/or activity.

As previously described, the electrode wires 920a-b are guided along the extension structure 922 and may be adhered to the extension structure 922 along certain portions of the electrode wire 920a-b. As shown in FIG. 9C, which depicts a reverse view of the cartridge electrode 425a-c, each electrode wire 920a-b can be individually attached to a conductive backing 925a-b such as a copper plate. Namely, as shown in the bottom-up view of the cartridge electrode 425a-c in FIG. 9D, each electrode wire 920a-b may be attached to a conductive backing 925a-b on the underside of the cartridge electrode 425a-c. Each conductive backing 925a-b is distinct (e.g., not in contact) from another conductive backing 925a-b. The analyzer console 140 can measure the impedance values of each electrode wire 920a-b by recording a measurement, such as a voltage reading, at each conductive backing 925a-b.

Referring now to the top down view of the cartridge electrode 425a-c depicted in FIG. 9E, the cartridge electrode forms an opening, hereafter termed the bead drop opening 930. The bead drop opening 930 is configured to substantially align with the bead drop inlet 805a-c of the cartridge body 405. As such, a reagent bead can enter into the mixing chamber 519a-c located beneath a cartridge electrode 425a-c by passing through the bead drop opening 930 and through the corresponding bead drop inlet 805a-c.

FIG. 10A depicts a cartridge slider 420, in accordance with an embodiment. As previously described, when the autoplatelet cartridge 120 is fully assembled, the cartridge slider 420 is situated within a cavity 450 of the cartridge body and is located below the overhang 630 of the left cover 410 and the overhang 715 of the right cover 415. Additionally, the cartridge slider 420 is located above the cartridge electrodes 425a-c and more specifically, able to slide over the platforms 910 of the cartridge electrodes 425a-c.

As depicted in FIG. 10A, the cartridge slider 420 includes one or more openings 1010a-c as well as one or more translational structures 1005a-b. Each opening 1010a-c may be configured to receive a reagent bead. As shown in FIG. 10A, each opening 1010a-c is a quadrilateral opening and as such, a spherical reagent bead can readily pass from a top side of the cartridge slider 420 through to the bottom side of the cartridge slider 420 by passing through the opening 1010a-c. In various embodiments, the cartridge slider 420 may be further structured to facilitate the entry of a reagent bead into an opening 1010a-c. For example, the walls adjacent to the openings 1010a-c may be slanted. Therefore, even if a reagent bead is not placed exactly over the opening 1010a-c, the adjacent walls guide the reagent bead to the opening 1010a-c.

The translational structures 1005a-b are configured to receive input, for example from the analyzer console 140, that causes the cartridge slider 420 to slide along the cavity 450 of the cartridge body 405. As an example, a first translational structure 1005a is located on the top side of the cartridge slider 420. As depicted in FIG. 10A, the first translational structure 1005a is a cylindrical structure with a hollow internal cavity. In various embodiments, the first translational structure 1005a is situated below the opening formed by the indentation 640 of the left cover 410 and the indentation 740 of the right cover 415. Therefore, the analyzer console 140 can apply a physical force (e.g., through a pin or a physical structure) that translates the cartridge slider 420 longitudinally (e.g., to the left or right) along the cavity 450 of the cartridge body 405. Additionally, a second translational structure 1005b on the cartridge slider 420 may be accessible through slider access port 710 of the right cover 415. In various embodiments, the second translational structure 1005b is a wall of the cartridge slider 420 that is adjacent to a gap. Therefore, the analyzer console 140 can access the second translational structure 1005b through the slider access port 710 and apply a physical force (e.g., through a pin or a physical structure) that translates the cartridge slider 420 longitudinally (e.g., to the left or right) along the cavity 450 of the cartridge body 405.

Reference is now made to FIG. 10B, which depicts a side view of the cartridge slider 420, in accordance with an embodiment. As depicted in FIG. 10B, the cartridge slider 420 includes one or more bosses 1020a-c that protrude from the surface of the cartridge slider 420. In various embodiments, the bosses 1020a-c are located on the cartridge slider 420 in order to correspond to the one or more divots 612a-c (see FIG. 6A) of the left cover. Namely, the height of each boss 1020a-c corresponds to the depth of the divot 612a-c. As such, the bosses 1020a-c can be in contact with the divots 612a-c in a neutral position (e.g., no forces between the cartridge slider 420 and overhang 630 of the left cover 410).

The cartridge slider 420 can transition between different positions within the cavity 450 to enable loading of reagent beads, holding of reagent beads, and dropping of reagent beads into the mixing chambers 519a-c. As described hereafter, the various positions will be referred to as the 1) bead loading position, 2) neutral position, 3) bead holding position, and 4) bead drop position.

In various embodiments, when the cartridge slider 420 is in the bead loading position, the cartridge slider 420 is in a position that is most distal to the sample well 122. Here, the openings 1010a-c of the cartridge slider 420 are aligned with the overhang openings 625a-c (see FIG. 6D) of the overhang 630 of the left cover 410. Therefore, reagent beads can be provided (e.g., by the analyzer console 140) through the overhang openings 625a-c and to the openings 1010a-c of the cartridge slider 425a-c. Additionally, each opening 1010a-c of the cartridge slider is aligned with a loading structure 940a-c of the cartridge body 405 (see FIG. 9A). More specifically, each of the loading structures 940a-c obstructs a reagent bead from fully passing through the openings 1010a-c of the cartridge slider 420. As such, when the cartridge slider 420 is in the bead loading position, reagent beads can be held within the openings 1010a-c of the cartridge slider 420 in contact with a loading structure 940a-c of the cartridge body 405. In various embodiments, to obstruct a reagent bead from passing through an opening 1010a-c of the cartridge slider 420, each loading structure 940a-c is located immediately below an opening 1010a-c of the cartridge slider 420. Namely, the distance between the loading structure 940a-c and the cartridge slider 420 is less than the size of a reagent bead such that the reagent bead is held within the opening 1010a-c of the cartridge slider 420 by the loading structure 940a-c.

The cartridge slider 420 may be translated to a neutral position. In various embodiments, the cartridge slider 420 is locally more proximal to the sample well 122 when in the neutral position as compared to when in the bead loading position. In various embodiments, when the cartridge slider 420 translates from the bead loading position to the neutral position, the reagent beads held within the openings 1010a-c of the cartridge slider correspondingly translate along with the cartridge slider 420.

When in the neutral position, the bosses 1020a-c of the cartridge slider correspond to the divots 612a-c (see FIG. 6A) of the left cover 410. As such, the bosses 1020a-c do not apply pressure to the overhang 630 of the left cover 410. Additionally, when the cartridge slider 420 is in the neutral position, the cartridge slider 420 serves to block the access from the overhang openings 625a-c to the cartridge electrodes 425a-c and the mixing chambers 519a-c. Therefore, the cartridge slider 420 may be placed in the neutral position when transporting or shipping the autoplatelet cartridge 120 to ensure stability of substances (e.g., fluid or magnetic stirrer) within the mixing chamber 519a-c.

The cartridge slider 420 may also be placed in a bead holding position. In various embodiments, the cartridge slider 420 is locally more proximal to the sample well 122 when in the bead holding position as compared to either the neutral position or the bead loading position. In various embodiments, when the cartridge slider 420 translates from the neutral position to the bead holding position, the reagent beads held within the openings 1010a-c of the cartridge slider 420 correspondingly translate along with the cartridge slider 420.

When in the bead holding position, each opening 1010a-c of the cartridge slider 420 is substantially aligned with a platform 910 of a cartridge electrode 425a-c located underneath the cartridge slider 420. As such, a reagent bead can be in contact with a platform 910 while still being held within the opening 1010a-c of the cartridge slider. In various embodiments, the distance between the platform 910 of a cartridge electrode 425a-c and the cartridge slider 420 is less than the size of a reagent bead such that the reagent bead is held within the opening 1010a-c of the cartridge slider 420 by the platform 910 of a cartridge electrode 425a-c.

The reagent bead may be held in this position while the mixing solution in the mixing chamber 519a-c is equilibrated. While in the bead holding position, each opening 1010a-c of the cartridge slider 420 does not align with the overhang openings 625a-c (see FIG. 6D) of the overhang 630 of the left cover 410, thereby enabling the reagent bead to remain within the autoplatelet cartridge 120 even if the orientation of the autoplatelet cartridge 120 is altered.

The cartridge slider 420 may also be placed in a bead drop position. In various embodiments, the cartridge slider 420 is locally more proximal to the sample well 122 when in the bead drop position as compared to any of the bead holding position, the neutral position, or the bead loading position. In various embodiments, when the cartridge slider 420 translates from the bead holding position to the bead drop position, the reagent beads held within the openings 1010a-c of the cartridge slider 420 correspondingly translate along with the cartridge slider 420.

When in the bead drop position, each opening 1010a-c of the cartridge slider 420 is substantially aligned with the bead drop opening of the cartridge electrode 425a-c as well as the bead drop inlet 805a-c of the cartridge body 405. As such, when the cartridge slider 420 is translated to the bead drop position from the bead holding position, a reagent bead can be dropped from the platform 910 of the cartridge electrode 425a-c into the mixing chamber 519a-c.

FIG. 11A-11B each illustrates a cutaway view of an assembled autoplatelet cartridge 120 as a reagent bead enters into a mixing chamber 519a-c, in accordance with an embodiment. More specifically, FIG. 11A-B each depicts a cutaway view (section L-L) as shown in FIG. 8B. FIG. 11A shows the presence of a reagent bead 1110 when the cartridge slider 420 is in the bead holding position. Namely, the reagent bead 1110 is held in contact with the platform 910 of the cartridge electrode 425a-c. Furthermore, FIG. 11A depicts the sealing structure 915 of the cartridge 425a-c which seals the mixing fluid within the mixing chamber 522a. Additionally, the extension structure 922 of the cartridge electrode 425a-c extends into the mixing chamber 519a-c. In various embodiments, the extension structure 922 remains a threshold distance away from the bottom of the mixing chamber 519a-c. This enables a mixing device to mix the fluid without adversely disrupting the measurements detected by the electrode wires 920a-b on the extension structure 922.

FIG. 11B depicts the position of the reagent bead 1110 immediately after the cartridge slider 420 is translated to the bead drop position. Namely, the reagent bead 1110 is dropped into the bead inlet 805a. Thus, the reagent bead 1110 can be mixed with the fluid within the mixing chamber 519a-c.

The reagent bead may be one of various types of platelet activators. For example, a reagent bead may be one or a combination of adenosine diphosphate (ADP), prostaglandin-E1, COX-1, arachidonic acid, Thrombin receptor-activating peptide (TRAP), and collagen. Although FIGS. 11A and 11B were described in reference to one reagent bead, more than one reagent bead may be provided to a mixing chamber 519a-c for determination of platelet activity.

Process of Testing Platelets

FIG. 12A-C illustrates a flow process of testing platelet behavior using the autoplatelet cartridge 120, in accordance with an embodiment. A blood sample 10 can be inserted 1205 into a blood receptacle (e.g., sample well 122) of the autoplatelet cartridge 120. Here, the autoplatelet cartridge 120 is inserted or may already be inserted into a cartridge port 150 of the analyzer console 140. Saline is released 1210 into the ampoule chamber 550 of the autoplatelet cartridge 120. In one embodiment, the saline may be originally housed within the ampoule 408 and situated within the ampoule chamber 550. The analyzer console 140 may provide an external force through the ampoule access port 545 in order to release the saline from the ampoule 408. The ampoule chamber 550 is then vented 1215 to ensure that air can flow into the ampoule chamber 550 to displace the saline. The ampoule chamber 550 can be vented through vent port 540 located in the ampoule chamber 550.

Saline is flowed 1220 through the fluid channels and into each measuring chamber 518-c of the autoplatelet cartridge 120. To do so, a vacuum can be applied to the vacuum pressure port 535 that draws the saline through appropriate fluid channels. Here, the autoplatelet cartridge 120 is in the following configuration: vent port 540 is open, vent seat 510 is closed, vent seat 515 is open, vent seat 520a-c are each closed, vent seat 525 is open, a vacuum is applied to vacuum pressure port 535. Thus, saline can be flowed through fluid channel 560, 564, 566, 568, and 570 in filling each measuring chamber 518a-c. The analyzer console 140 may detect 1225 that saline has filled each measuring chamber 518a-c to capacity. As an example, the analyzer console 140 may detect the presence of saline at fluid detection location 730b. Detection of saline at fluid detection location 730b means that saline has filled each of the measuring chambers 518a-c.

Saline in each measuring chamber 518a-c is displaced 1230 into a corresponding mixing chamber 519a-c. To accomplish this, the autoplatelet cartridge 120 adopts the following configuration: vent port 540 is closed, vent seat 510 is closed, vent seat 515 is closed, vent seat 520a-c are each opened, vent seat 525 is closed, a positive pressure is applied to input pressure port 530. In various embodiments, the saline in each measuring chamber 518a-c is displaced in sequential fashion. Namely, a vent seat 520c is the first among vent seats 520a-c that is opened when the positive pressure is applied to input pressure port 530. Thus, saline in measuring chamber 518c is displaced into mixing chamber 519c. Subsequently, vent seat 520c is closed and vent seat 520b is opened. Thus, saline in measuring chamber 518b is displaced into mixing chamber 519b. Subsequently, vent seat 520b is closed and vent seat 520a is opened. Thus, saline in measuring chamber 518a is displaced into mixing chamber 519a. Vent seat 520a is then closed. In various embodiments, the volume of saline displaced into each mixing chamber 519a-c is 150 µL. Additionally, a mixing device (e.g., magnetic stirrer) may rotatably stir the saline in the mixing chamber 519a-c while the analyzer console 140 heats the saline to a predetermined temperature (e.g., 37° C.).

After saline is displaced into each mixing chamber 519a-c, the saline that remains within the fluid channels of the autoplatelet cartridge 120 is eliminated 1235. To accomplish this, the autoplatelet cartridge 120 adopts the following configuration: vent port 540 is open, vent seat 510 is closed, vent seat 515 is open, vent seat 520a-c are each closed, vent seat 525 is open, a vacuum is applied to vacuum pressure port 535. Thus, saline is drawn into waste chamber 590.

After saline is removed from the fluid channels, the blood from the blood sample 10 is flowed 1240 through the fluid channels into each of the measuring chambers 518a-c. Here, the autoplatelet cartridge 120 is in the following configuration: vent port 540 is closed, vent seat 510 is open, vent seat 515 is closed, vent seat 520a-c are each closed, vent seat 525 is open, a vacuum is applied to vacuum pressure port 535. Thus, blood can be flowed through fluid channel 562, 564, 566, 568, and 570 in filling each measuring chamber 518a-c. Similar to the detection of saline as previously described, the analyzer console 140 may detect 1245 that blood has filled each measuring chamber 518a-c to capacity. As an example, the analyzer console 140 may detect the presence of blood at fluid detection location 730b.

The blood in each measuring chamber 518a-c is displaced 1250 into the corresponding mixing chamber 519a-c where the saline is currently mixing. To accomplish this, the autoplatelet cartridge 120 adopts the following configuration: vent port 540 is closed, vent seat 510 is closed, vent seat 515 is closed, vent seat 520a-c are each opened, vent seat 525 is closed, a positive pressure is applied to input pressure port 530. In various embodiments, the blood in each measuring chamber 518a-c is displaced in sequential fashion. Namely, a vent seat 520c is the first among vent seats 520a-c that is opened when the positive pressure is applied to input pressure port 530. Thus, blood in measuring chamber 518c is displaced into mixing chamber 519c. Subsequently, vent seat 520c is closed and vent seat 520b is opened. Thus, blood in measuring chamber 518b is displaced into mixing chamber 519b. Subsequently, vent seat 520b is closed and vent seat 520a is opened. Thus, blood in measuring chamber 518a is displaced into mixing chamber 519a. Vent seat 520a is then closed. In various embodiments, the volume of blood displaced into each mixing chamber 519a-c is 150 µL and allowed to mix 1255 with the saline in the mixing chamber 519a-c. As such, the mixture of fluid in the mixing chamber 519a-c is a 1:1 ratio of blood and saline (e.g., 150 µL of each type of fluid). In various embodiments, the ratio of the two fluids can be altered and need not be precisely a 1:1 ratio. Additionally, a mixing device (e.g., magnetic stirrer) may rotatably stir the fluid mixture in the mixing chamber 519a-c while the analyzer console 140 heats the mixture to a predetermined temperature (e.g., 37° C.).

The remaining blood in the fluid channels of the autoplatelet cartridge 120 is eliminated 1260. To accomplish this, the autoplatelet cartridge 120 adopts the following configuration: vent port 540 is open, vent seat 510 is closed, vent seat 515 is open, vent seat 520a-c are each closed, vent seat 525 is open, a vacuum is applied to vacuum pressure port 535. Thus, blood is drawn into waste chamber 590.

Although FIGS. 12A and 12B depict a particular flow process, in various embodiments, the autoplatelet cartridge 120 may first displace blood into the mixing chambers 519a-c (e.g., steps 1240-1260 in FIG. 12B) and subsequently mix saline into the mixing chambers 519a-c (e.g., steps 1210-1235 in FIG. 12A).

Referring now to FIG. 12C, for each mixing chamber 519a-c of the autoplatelet cartridge 120, the autoplatelet cartridge 120 receives 1270 one or more reagent beads through a cartridge slider 420. As an example, the reagent beads may be inserted through the overhang openings 625a-c of the left cover 410 into a corresponding opening 1010a-c of the cartridge slider 420. In various embodiments, the reagent beads are provided by the analyzer console 140. In other embodiments, the reagent beads may be pre-loaded into the cartridge slider while the cartridge slider 420 is in the bead loading position.

The saline and blood mixture is equilibrated 1265. Namely, the analyzer console 140 may deem each solution mixture equilibrated if the impedance measurement detected by the cartridge electrode 425a-c (through the electrode wires 920a-b) remains within a threshold deviation range for a threshold amount of time. Additionally, the analyzer console 140 may include a temperature sensor that ensures that the temperature of the mixing solution in the mixing chamber 519a-c is also remaining within a threshold deviation range for a threshold amount of time. In various embodiments, the cartridge slider 420 may be translated to a bead holding position such that the provided reagent beads are held on the platform 910 of a cartridge electrode 425a-c while the solution is equilibrated.

Once the mixing solution in each mixing chamber 519a-c is equilibrated, the one or more reagent beads are provided 1275 to the equilibrated mixture in the mixing chamber 519a-c. For example, the cartridge slider 420 may transition from the bead holding position to the bead drop position. The cartridge slider 420 may transition in response to an external force input provided by the analyzer console 140. In some embodiments, the mixing solution is held for a threshold period of time to ensure that the reagent bead fully dissolves within the mixing chamber 519a-c.

After adding the reagent beads, the analyzer console 140 may measure 1280 impedance changes within the mixture due to the provided one or more reagent beads. In various embodiments, each mixing chamber is provided a different reagent bead that provides a different measurable of platelet activity. For example, the reagent bead may cause platelet aggregation on the electrode wires 920a-c of the cartridge electrode 425a-c. As such, the analyzer console 140 may determine 1285 platelet activity of the blood sample based on the measured impedance changes.

Computing System

FIG. 13A-B illustrate an overview of the analyzer console 140, in accordance with an embodiment. Referring to FIG. 13a, the main chassis 144 of the analyzer console 140 can include a front portion 144f and a rear portion 144b. In some embodiments, the rear portion 144b houses at least some of the computer and electronic components that are necessary for the operations of the analyzer console 140. For example, the rear portion 144b can house hardware devices and software such as, but not limited to, computer processors, memory devices, an operating system and other executable instructions, power source(s), user interface controls, communication devices, circuit boards, and the like.

In the depicted embodiment, the front portion 144f includes a cover 1345 and a sample handler assembly 1300. The sample handler assembly 1300 defines an interior space in which the cartridge 120 can be received. In some embodiments, the sample handler assembly 1300 is a modular sub-assembly of the analyzer console 140, and the sample handler assembly 1300 can be readily removed from the analyzer console 140 for service. The sample handler assembly 1300 is electrically interconnected with the computer and electronic components that are housed in the rear portion 144b. As such, the analyzer console 140 can perform testing on a blood sample located in cartridge 120 and display the results on the touchscreen display 142.

Referring now to FIG. 13B, the analyzer console 140 can include a cartridge receiver and clamp 1310 and a platelet activity measurement system 1380. A mechanical frame assembly is used to support the cartridge receiver and clamp 1310 and the platelet activity measurement system 1380 in orientations such that the cartridge receiver and clamp 1310 and the viscoelastic measurement system 1380 can function symbiotically.

Portions of the cartridge receiver and clamp 1310 and the platelet activity measurement system 1380 are moveable in relation to the mechanical frame assembly (which is stationary in relation to the analyzer console 140). For example, the platelet activity measurement system 1380 can move upward and downward. As will be described further below, the platelet activity measurement system 1380 can move downward to engage with the cartridge 120 (e.g., refer to FIG. 13A), and upward to disengage from the cartridge 120. A portion of the cartridge receiver and clamp 1310 can move horizontally in relation to the mechanical frame assembly.

As will be described further below, a portion of the cartridge receiver and clamp 1310 can move horizontally to clamp or unclamp the cartridge 120 within the sample handler assembly 1300.

In some embodiments, the cartridge receiver and clamp 1310 includes a movable block sub-assembly and a stationary block sub-assembly. A space exists between the movable block sub-assembly and the stationary block sub-assembly in which the cartridge 120 can be received. The movable block sub-assembly can be translated towards or away from the stationary block sub-assembly. Accordingly, the cartridge 120 can be clamped and unclamped between the movable block sub-assembly and the stationary block sub-assembly by virtue of the relative movement therebetween. In some embodiments, the platelet activity measurement system 1380 is mounted to the movable block sub-assembly. Therefore, as the movable block sub-assembly is translated, the platelet activity measurement system 1380 is also translated.

In some embodiments, the moveable block sub-assembly can be translated by an electric motor. In particular embodiments, the motor is a stepper motor. In some embodiments, a gear reducer is coupled to the motor. Using a belt and pulley arrangement for compactness, the motor can be used to drive a lead screw. The threads of the lead screw can be engaged with complementary threads of the movable block such that a rotation of the lead screw results in horizontal translation of the movable block. In some embodiments, end-of-travel detectors (e.g., proximity sensors, optical sensors, micro-switches, and the like) are included to detect when the moveable block sub-assembly has been horizontally translated to the desired end-of-travel positions.

In some embodiments, one or more springs can extend between the movable moveable block sub-assembly and the stationary block sub-assembly. The springs can help facilitate a suitable clamping force between the movable block sub-assembly and the stationary block sub-assembly. In some embodiments, the springs are adjustable.

In some embodiments, portions of the moveable block sub-assembly and the stationary block sub-assembly that make contact with the cartridge 120 comprise a flexible or compressible material so that while the cartridge 120 is clamped it is also protected from damage.

In some embodiments, one or both of the moveable block sub-assembly and the stationary block sub-assembly include heating devices 1312 that can warm the cartridge 120 when the cartridge 120 is clamped therebetween. For example, in some embodiments the heaters 1312 are electrical resistance heaters that are used to heat at least portions (e.g., mixing chamber 519a-c) of the cartridge 120 to a predesignated temperature (e.g., 37°). In some embodiments, the heaters 1312 are configured to facilitate warming of individual portions of the cartridge 120 independently from other portions of the cartridge 120. For example, one or more of the individual fluid channels 560, 562, 564, 566, 568, 570, 572, and 580a-c (see FIG. 5A) can be independently warmed in some such embodiments. Warming may be performed to one or more sides of the cartridge 120. Other types of warming modalities may be used including, but not limited to, IR, ultrasonic, microwave, and the like.

In particular embodiments, one or more temperature sensors 1314 are included that can detect the temperature of the cartridge 120 at one or more locations on the cartridge 120. For example, in some embodiments the one or more temperature sensors 1314 can be thermocouples, thermistors, infra-red temperature sensors, and the like. Accordingly, the analyzer console 140 can control the heating of the cartridge 120 to a predetermined temperature (e.g., about 37° C.) using the heaters 1312 and the temperature sensors 1314.

The moveable block sub-assembly can include multiple solenoids that are used to actuate the aforementioned vents and valves of the cartridge 120. For example the valve structures 605a-f can be actuated by valve actuators 1330 and the vent port 540 can be actuated by vent actuators 1332. In some embodiments, the valve actuators 1330 and the vent actuators 1332 comprise solenoids. Actuation of the valve structures 605a-f by the valve actuators 1330 can be accomplished by coupling pins to the valve actuators 1330 that are extendable from the moveable block sub-assembly to make contact with and to distend valve elastomer members so that the elastomer members make contact with a valve seat within the cartridge 120. Actuation of the vent port 540 by the vent actuators 1332 can be accomplished by coupling pins with resilient tips that are extendable from the moveable block sub-assembly to obstruct the vent port 540. Such pins with resilient tips can act as stoppers to substantially prevent airflow through the vent port 540. In some embodiments, the valve actuators 1330 and the vent actuators 1332 comprise solenoids that include internal springs that cause the valve actuators 1330 and the vent actuators 1332 to be normally extended (e.g., when the electrical power is removed from the solenoids). Accordingly, such normally closed solenoids will close the vents and valves of the cartridge 120 as a default configuration.

The sample handler assembly 1300 also includes pressure source 1336 and vacuum source 1334 by which air pressure and vacuum can be applied to the input pressure port 530 and vacuum pressure port 535 of autoplatelet cartridge 120 respectively. For example, the pressure source 1336 and vacuum source 1334 can make contact with the cartridge 120 and can convey pressure or vacuum to the input pressure port 530 and vacuum pressure port 535 when the cartridge 120 is clamped within the cartridge receiver and clamp 1310. The pressure source 1336 and vacuum source 1334 are at least partially made of a resilient material in some embodiments. For example, in some embodiments the pressure source 1336 and vacuum source 1334 are at least partially made of a resilient material such as, but not limited to, silicone, butyl rubber, nitrile rubber, ethylene propylene rubber, fluoroelastomers, and the like. One or more internally-housed pressure and/or vacuum pumps (not shown) can also be included in the analyzer console 140. Such internally-housed pressure and vacuum pumps can be used to generate the air pressure or vacuum that is applied to the cartridge 120 to induce the transport of fluid within the autoplatelet cartridge 120 as described above.

As previously described, the cartridge receiver and clamp 1310 also includes the stationary block sub-assembly. In some embodiments, the stationary block sub-assembly does not move in relation to the mechanical frame assembly and in relation to the analyzer console 140 as a whole.

In some embodiments, the analyzer console 140 includes a mixing unit 1340. In particular embodiments, the mixing unit 1340 includes a motor, a crank and connecting rod assembly, and a magnet shuttle. These components can be used to magnetically couple with the mixing elements (e.g., magnetic stirrer) of the autoplatelet cartridge 120 and to induce movement of the mixing elements within the mixing chambers 519a-c. The movement of the mixing elements encourages the reagent beads to dissolve in the mixing fluid contained within the mixing chambers 519a-c as described above.

The analyzer console 140 can also include one or more sensors 1348. The one or more sensors 1348 can be used to detect the presence of fluid in particular locations within the cartridge 120, such as fluid detection locations 127a and 730a-b as described above. In some embodiments, the sensors 1348 are optical sensors, such as IR (infrared) sensors. In some embodiments, the sensors 1348 can be used to detect fluid in other areas of the cartridge 120.

The sample handler assembly 1300 of the analyzer console 140 also includes the platelet activity measurement system 1380. In various embodiments, the platelet activity measurement system 1380 may include one or more assemblies that provides a physical input to the ampoule 408 within the autoplatelet cartridge 120 through ampoule access port 545. As an example, the physical input may be provided by a structure that extends through the ampoule access port 545 and physically impacts the ampoule 408. As another example, the physical input may be an alternative means of energy such as an ultrasound application. The platelet activity measurement system 1380 may further include one or more assemblies that include a structure that provides a physical input to the translational structures 1005a-b of the cartridge slider 420 in order to translate the cartridge slider 420 to various positions. The platelet activity measurement system 1380 may further include various wire leads that are configured to contact the contact pads 925a-b of each cartridge electrode 425a-c in order to obtain the impedance measurement detected by the corresponding electrode wires 920a-b.

In addition to the aforementioned features of the analyzer console 140, in some embodiments the analyzer console 140 also includes one or more of the following features. The analyzer console 140 can include one or more barcode scanners 1350 that, for example, can read a barcode on the autoplate cartridge 120. In some embodiments, the analyzer console 140 can include one or more devices to detect the presence of the cartridge 120 in a desired insertion location and/or orientation. For example, in some embodiments one or more micro switches can be used to detect when the cartridge 120 has been inserted in a desired location and orientation within the sample handler assembly 1300. In some embodiments, the analyzer console 140 can include one or more auxiliary connections 1360. The auxiliary connections 1360 can include network and device connectors such as, but not limited to, one or more USB ports, Ethernet ports (e.g., RJ45), VGA connectors, Sub-D9 connectors (RS232), and the like. Such auxiliary connections 1360 can be located on the rear of the main chassis 144, or at other convenient locations on the main chassis 144. For example, in some embodiments one or more USB ports may be located on or near the front of the main chassis 144.

The analyzer console 140 also includes a user interface 142 (e.g., with a touchscreen display in this embodiment). In the depicted embodiment, the user interface 142 is configured to receive user input and to display output information to the user. For example, the user can enter information to the analyzer console 140 by making selections of various soft-buttons that may be displayed on the user interface 142 at times during the beginning, middle, and end of the testing process. In some embodiments, other selections such as, but not limited to, soft keyboard entries can be provided via user interface 142. In some embodiments, data entry can be performed additionally or alternatively by voice entry. In some embodiments, the user interface may include other peripheral devices (e.g., a mouse, a keyboard, an additional display device, and the like) as part of the analyzer console 140. In some embodiments, a computer data network (e.g., intranet, internet, LAN, etc.) may be used to allow for remote devices to receive and/or input information from the system 100. For example, in some embodiments one or more remote displays can be utilized via auxiliary connections 1360. In the depicted embodiment, the user interface 142 also includes an external barcode reader. Alternatively or additionally, the user interface 142 of the analyzer console 140 can be equipped with a reader configured to read near-field communication tags, RFID tags, or the like. The analyzer console 140 can also include one or more control systems 1370 that can execute instructions embodied in a computer program. The control systems 1370 can include, by way of example, both general and special purpose microprocessors, and any one or more processors of any kind of digital computer. In some embodiments, the control systems 1370 includes one or more such processors, memory, storage devices, interfaces, and other types of electronic sub-systems and components. Such components may be mounted on a common motherboard or in other manners as appropriate. The control systems 1370 can process instructions for execution within the analyzer console 140, including instructions stored in the memory or on the storage device. In some implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The storage devices are capable of providing mass storage for the control systems 1370. In some implementations, the storage device may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The computer program product can also be tangibly embodied in a computer- or machine-readable medium, such as the memory, the storage device, or memory on the processor(s).

Additional Embodiment Considerations

Throughout this specification, as used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Finally, as used herein any reference to "one embodiment," "some embodiments," or "various embodiments" means that a particular element, feature, structure, or characteristic described in connection with the embodiment is included in at least one embodiment. The appearances of the phrase "in one embodiment" in various places in the specification are not necessarily all referring to the same embodiment.

Upon reading this disclosure, those of skilled in the art will appreciate still additional alternative structural and functional designs for propeller blades as disclosed from the principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement and details of the apparatus disclosed herein without departing from the spirit and scope defined in the appended claims.

What is claimed is:

1. A cartridge device for testing platelet activity in a blood sample comprising:
    a cartridge body comprising:
        a measuring chamber configured to contain a defined volume of fluid;
        a mixing chamber in fluid communication with the measuring chamber through a duct that further comprises a valve seat, the mixing chamber further comprising an inlet for receiving a reagent bead; and
        a cavity located on a top surface of the cartridge body;
    a left cover coupled to the cartridge body, the left cover comprising:
        a valve structure configured to couple with the valve seat of the cartridge body and block fluid flow between the measuring chamber and mixing chamber;
    a cartridge slider comprising an opening configured to receive the reagent bead, the cartridge slider located within the cavity of the cartridge body; and
    a cartridge electrode configured to couple with the cartridge body, the cartridge electrode comprising:
        an extension structure; and
        one or more electrode wires coupled to the extension structure, wherein a portion of the one or more electrode wires are situated within the mixing chamber of the cartridge body when the cartridge electrode is coupled with the cartridge body.

2. The cartridge device of claim 1 further comprising:
    a right cover coupled to the cartridge body, the right cover comprising one or more access ports enabling access to the cartridge slider.

3. The cartridge device of claim 1, wherein the left cover further comprises:
    a bead opening on a top surface of the left cover, the bead opening aligned with the inlet of the mixing chamber.

4. The cartridge device of claim 1, wherein the valve structure comprises an elastomeric member.

5. The cartridge device of claim 4, wherein the elastomeric material of the valve structure deforms in response to an external input to couple with the valve seat of the cartridge body.

6. The cartridge device of claim 1, wherein the cartridge body further comprises:
    an ampoule chamber that further comprises a hermetically sealed container, wherein the ampoule chamber is in fluid communication with the measuring chamber through a fluid channel.

7. The cartridge device of claim 6, wherein the cartridge body further comprises an access port that is configured to receive an external input, wherein the external input causes the hermetically sealed container to release a fluid into the ampoule chamber.

8. The cartridge device of claim 6, wherein the cartridge body further comprises:
    a sample well configured to receive a blood sample;
    a second valve seat located between the ampoule chamber and the fluid channel, wherein the second valve seat, when open, enables fluid flow between the ampoule chamber and the fluid channel; and
    a third valve seat located between the sample well and the fluid channel, wherein the third valve seat, when open, enables fluid flow between the sample well and the fluid channel.

9. The cartridge device of claim 1, wherein the cartridge body further comprises:
    a second measuring chamber configured to contain a second defined volume of fluid; and a third measuring chamber configured to contain a third defined volume of fluid,
    wherein the third measuring chamber is in fluid communication with the second measuring chamber, and wherein the second measuring chamber is in fluid communication with the measuring chamber.

10. The cartridge device of claim 1, wherein the cartridge electrode further comprises:
    a platform comprising an elastomer material surface; and
    a sealing structure configured to seal a fluid within the mixing chamber of the cartridge body.

11. The cartridge device of claim 10, wherein the cartridge electrode further comprises:
    an opening adjacent to the platform, wherein the opening of the cartridge electrode is aligned with the inlet of the mixing chamber of the cartridge body.

12. The cartridge device of claim 10, wherein the sealing structure comprises a sealing surface that is one of a rubber O-ring or a hydrophobic surface coating.

13. The cartridge device of claim 1, wherein the cartridge body further comprises a loading structure, and wherein the opening of the cartridge slider is aligned with the loading structure of the cartridge body when the cartridge slider is in a first position.

14. The cartridge device of claim 1, wherein the cartridge slider further comprises
    a boss elevated from a surface of the cartridge slider, the boss configured to couple with a divot on the left cover when the cartridge slider is in a second position.

15. The cartridge device of claim 1, wherein the opening of the cartridge slider is aligned with a platform of the cartridge electrode when the cartridge slider is in a third position.

16. The cartridge device of claim 1, wherein the opening of the cartridge slider is aligned with the inlet of the mixing chamber of the cartridge body when the cartridge slider is in a fourth position.

17. A method of testing platelet activity in a blood sample using the cartridge device of claim 1, the method comprising:
    flowing a first fluid into the measuring chamber;
    displacing the first fluid from the measuring chamber into the mixing chamber;
    flowing a second fluid into the measuring chamber;
    displacing the second fluid from the measuring chamber into the mixing chamber to mix with the first fluid;
    translating the cartridge slider to a position within the cavity of the cartridge body to provide a reagent bead to the mixing chamber; and determining platelet activity of the blood sample based on measurements taken from a mixture of the first and second fluids in the mixing chamber by the cartridge electrode of the cartridge device.

18. The method of claim 17, wherein the first fluid is saline and the second fluid is a portion of the blood sample.

19. The method of claim 17, wherein the first fluid and second fluid are mixed in the mixing chamber at equal volumes.

20. The method of claim 17, wherein the measurements taken by the cartridge electrode comprise impedance changes over time.

* * * * *